US00RE46617E

(19) United States
(12) Reissued Patent
Hanselmann et al.

(10) Patent Number: US RE46,617 E
(45) **Date of Reissued Patent: *Nov. 28, 2017**

(54) PROCESS FOR MAKING QUINOLONE COMPOUNDS

(71) Applicant: Melinta Therapeutics, Inc., New Haven, CT (US)

(72) Inventors: Roger Hanselmann, Branford, CT (US); Maxwell M. Reeve, Guilford, CT (US); Graham Johnson, Madison, CT (US)

(73) Assignee: MELINTA THERAPEUTICS, INC., New Haven, CT (US)

( * ) Notice: This patent is subject to a terminal disclaimer.

(21) Appl. No.: 14/743,365

(22) Filed: Jun. 18, 2015

Related U.S. Patent Documents

Reissue of:
(64) Patent No.: 8,497,378
Issued: Jul. 30, 2013
Appl. No.: 13/120,278
PCT Filed: Sep. 23, 2009
PCT No.: PCT/US2009/005276
§ 371 (c)(1),
(2) Date: Nov. 1, 2011
PCT Pub. No.: WO2010/036329
PCT Pub. Date: Apr. 1, 2010

U.S. Applications:
(60) Provisional application No. 61/194,083, filed on Sep. 24, 2008.

(51) Int. Cl.
*C07D 215/38* (2006.01)
*C07D 401/14* (2006.01)

(52) U.S. Cl.
CPC ..... *C07D 401/14* (2013.01)

(58) Field of Classification Search
CPC ..... C07D 401/14
USPC ..... 546/159
See application file for complete search history.

(56) References Cited

U.S. PATENT DOCUMENTS 5,998,436 A 12/1999 Yazaki et al.
8,497,378 B2 7/2013 Hanselmann et al.

FOREIGN PATENT DOCUMENTS

WO 2006-015194 * 2/2006
WO WO-2006/015194 A2 2/2006
WO WO-2006015194 A2 2/2006
WO WO-2006/042034 A2 4/2006
WO WO-2006/110815 A1 10/2006
WO WO-2006110815 A1 10/2006

OTHER PUBLICATIONS

Mealy, N.E. et al. "ABT-492", Drugs of the Future 2002, 27(11), 1033-1038.
Barnes, D.M. et al. "Chlorination at the 8-Position of a Functionalized Quinolone and the Synthesis of Quinolone Antibiotic ABT-492," Organic Process Research & Development 2006, 10, 803-807.
Hanselmann, R. et al. "Identification and Suppression of a Dimer Impurity in the Development of Delafloxacin," Organic Process Research & Development 2009, 13, 54-59.
Barnes, Org Process Res & Dev, vol. 10, pp. 803-807, 2006.*
Haight, Org Process Res & Dev, vol. 10, pp. 751-756, 2006.*
Extended European Search Report dated Jun. 1, 2012 for corresponding European Patent Application No. 09816565.7 (4 pages).
Haight, A.R. et al., "Synthesis of the Quinolone ABT-492: Crystallizations for Optimal Processing," Organic Process Research & Development 2006, 10, 751-756.
International Search Report and Written Opinion dated May 6, 2010 for corresponding International Patent Application No. PCT/US2009/005276 (13 pages).

* cited by examiner

*Primary Examiner* — Dwayne C. Jones
(74) *Attorney, Agent, or Firm* — Wilmer Cutler Pickering Hale and Dorr LLP

(57) ABSTRACT

The present invention relates to the field of synthesizing anti-infective compounds. More particularly, the invention relates to synthesizing a family of quinolone compounds useful as anti-infective agents. The invention includes a process for preparing a quinolone compound wherein less than about 0.40% of dimeric impurity of the quinolone is produced.

19 Claims, 14 Drawing Sheets

Experimental Table

Initial Design of Experiment

| Experiment | Pattern | NCS (equivalents) | Sulfuric acid (mol%) | Temp. (C) | Solvent (volume) | Water in solvent (%) | NCS addition rate (vol/min) | Solvent | 4 after 5h (area%) |
|---|---|---|---|---|---|---|---|---|---|
| 1 | −−++−−+ | 1.05 | 2 | 25 | 3 | 0 | 0.05 | MeOAc | 0.239 |
| 2 | ++−−++− | 1.2 | 5 | 15 | 2 | 0.5 | 0.3 | EtOAc | 0.05 |
| 3 | −++−−++ | 1.05 | 5 | 25 | 2 | 0 | 0.3 | MeOAc | 0.139 |
| 4 | 2 | 1.125 | 3.5 | 20 | 2.5 | 0.25 | 0.175 | MeOAc | 0.247 |
| 5 | +−−++−− | 1.2 | 2 | 15 | 3 | 0.5 | 0.05 | EtOAc | 0.068 |
| 6 | −+−+−+− | 1.05 | 5 | 15 | 3 | 0 | 0.3 | EtOAc | 0.095 |
| 7 | +++−−−− | 1.2 | 5 | 25 | 2 | 0 | 0.05 | EtOAc | 0.125 |
| 8 | 1 | 1.125 | 3.5 | 20 | 2.5 | 0.25 | 0.175 | EtOAc | 0.192 |
| 9 | −+−−+−+ | 1.05 | 5 | 15 | 2 | 0.5 | 0.05 | MeOAc | 0.234 |
| 10 | −−−−−−− | 1.05 | 2 | 15 | 2 | 0 | 0.05 | EtOAc | 0.185 |
| 11 | −−+−++− | 1.05 | 2 | 25 | 2 | 0.5 | 0.3 | EtOAc | 0.475 |
| 12 | +−++−+− | 1.2 | 2 | 25 | 3 | 0 | 0.3 | EtOAc | 0.123 |
| 13 | +−+−+−+ | 1.2 | 2 | 25 | 2 | 0.5 | 0.05 | MeOAc | 0.322 |
| 14 | +−−−−++ | 1.2 | 2 | 15 | 2 | 0 | 0.3 | MeOAc | 0.129 |
| 15 | ++−+−−+ | 1.2 | 5 | 15 | 3 | 0 | 0.05 | MeOAc | 0.168 |
| 16 | −−−++++ | 1.05 | 2 | 15 | 3 | 0.5 | 0.3 | MeOAc | 0.11 |
| 17# | 1 | 1.125 | 3.5 | 20 | 2.5 | 0.25 | 0.175 | EtOAc | 0.372 |
| 18 | +++++++ | 1.2 | 5 | 25 | 3 | 0.5 | 0.3 | MeOAc | 0.472 |
| 19 | −++++−− | 1.05 | 5 | 25 | 3 | 0.5 | 0.05 | EtOAc | 0.68 |

#Experiment 17 was deemed an outlier and was ignored for the analysis

FIG.4

| Summary of Fit | |
|---|---|
| RSquare | 0.9965 |
| RSquare Adj | 0.985126 |
| Root Mean Square Error | 0.020258 |
| Mean of Response | 0.225167 |
| Observations (or Sum Wgts) | 18 |

| Analysis of Variance | | | | |
|---|---|---|---|---|
| Source | DF | Sum of Squares | Mean Square | F Ratio |
| Model | 13 | 0.46741489 | 0.035955 | 87.6090 |
| Error | 4 | 0.00164161 | 0.00410 | Prob>F |
| C. Total | 17 | 0.46905650 | | 0.0003* |

| Parameter Estimates | | | | |
|---|---|---|---|---|
| Term | Estimate | Std Error | t Ratio | Prob>\|t\| |
| Intercept | 0.2251667 | 0.004775 | 47.16 | <.0001* |
| NCS (equivalents)(1.05,1.2) | −0.04375 | 0.005065 | −8.64 | 0.0010* |
| Sulfuric acid (mol%)(2,5) | 0.0195 | 0.005065 | 3.85 | 0.0183* |
| Temperature (C)(15,25) | 0.096 | 0.005065 | 18.96 | <.0001* |
| Solvent (vol)(2,3) | 0.0185 | 0.005065 | 3.65 | 0.0217* |
| Water in Solvent (%)(0,0.5) | 0.0755 | 0.005065 | 14.91 | 0.0001* |
| NCS addition rate (vol/min)(0.05,0.3) | −0.02675 | 0.005065 | −5.28 | 0.0062* |
| Solvent[EtOAc] | −0.003722 | 0.004775 | −0.78 | 0.4792* |
| NCS (equivalents)*Temperature (C) | −0.017625 | 0.005065 | −3.48 | 0.0254* |
| NCS (equivalents)*Solvent (vol) | 0.007125 | 0.005065 | 1.41 | 0.2322* |
| NCS (equivalents)*Water in Solvent (%) | −0.029625 | 0.005065 | −5.85 | 0.0043* |
| NCS (equivalents)*NCS addition rate (vol/min) | 0.038125 | 0.005065 | 7.53 | 0.0017* |
| NCS (equivalents)*Solvent[EtOAc] | −0.089875 | 0.005065 | −17.75 | <.0001* |
| Sulfuric acid (mol%)*Temperature (C) | 0.012625 | 0.005065 | 2.49 | 0.0673 |

FIG.5D

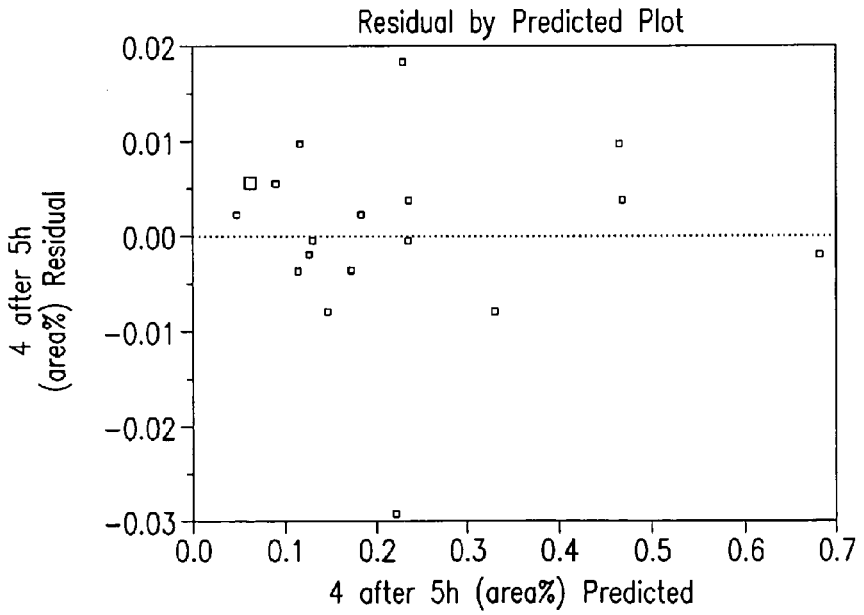

FIG.5E

Sorted Parameter Estimates

| Term | Estimate | Std Error | t Ratio | Prob>\|t\| |
|---|---|---|---|---|
| Temperature (C)(15,25) | 0.096 | 0.005065 | 18.96 | <.0001* |
| NCS (equivalents)*Solvent[EtOAc] | −0.089875 | 0.005065 | −17.75 | <.0001* |
| Water in Solvent (%)(0,0.5) | 0.0755 | 0.005065 | 14.91 | 0.0001* |
| NCS (equivalents)(1.05,1.2) | −0.04375 | 0.005065 | −8.64 | 0.0010* |
| NCS (equivalents)*NCS addition rate (vol/min) | 0.038125 | 0.005065 | 7.53 | 0.0017* |
| NCS (equivalents)*Water in Solvent (%) | −0.029625 | 0.005065 | −5.85 | 0.0043* |
| NCS addition rate (vol/min)(0.05,0.3) | −0.02675 | 0.005065 | −5.28 | 0.0062* |
| Sulfuric acid (mol%)(2,5) | 0.0195 | 0.005065 | 3.85 | 0.0183* |
| Solvent (vol)(2,3) | 0.0185 | 0.005065 | 3.65 | 0.0217* |
| NCS (equivalents)*Temperature (C) | −0.017625 | 0.005065 | −3.48 | 0.0254* |
| Sulfuric acid (mol%)*Temperature (C) | 0.012625 | 0.005065 | 2.49 | 0.0673 |
| NCS (equivalents)*Solvent (vol) | 0.007125 | 0.005065 | 1.41 | 0.2322 |
| Solvent[EtOAc] | −0.003722 | 0.004775 | −0.78 | 0.4792 |

FIG.5F

Robustness Design of Experiment

Experimental Table

| Experiment | Pattern | NCS (equivalents) | Temp. (C) | NCS addition rate (vol/min) | Sulfuric acid (mol%) | 4 (area%) |
|---|---|---|---|---|---|---|
| 1 | +−+− | 1.07 | 13 | 75 | 0.8 | 0.07 |
| 2 | 0 | 1.055 | 17 | 52.5 | 1 | 0.09 |
| 3 | −−−− | 1.04 | 13 | 30 | 0.8 | 0.09 |
| 4 | −+−+ | 1.04 | 21 | 30 | 1.2 | 0.09 |
| 5 | −−++ | 1.04 | 13 | 75 | 1.2 | 0.07 |
| 6 | ++++ | 1.07 | 21 | 75 | 1.2 | 0.07 |
| 7 | +−−+ | 1.07 | 13 | 30 | 1.2 | 0.07 |
| 8 | 0 | 1.055 | 17 | 52.5 | 1 | 0.08 |
| 9 | −++− | 1.04 | 21 | 75 | 0.8 | 0.1 |
| 10 | ++−− | 1.07 | 21 | 30 | 0.8 | 0.09 |

FIG.7

| Summary of Fit | |
|---|---|
| RSquare | 0.905172 |
| RSquare Adj | 0.82931 |
| Root Mean Square Error | 0.00469 |
| Mean of Response | 0.082 |
| Observations (or Sum Wgts) | 10 |

Analysis of Variance

| Source | DF | Sum of Squares | Mean Square | F Ratio |
|---|---|---|---|---|
| Model | 4 | 0.00105000 | 0.000262 | 11.9318 |
| Error | 5 | 0.00011000 | 0.000022 | Prob>F |
| C. Total | 9 | 0.00116000 | | 0.0090* |

| Lack Of Fit | | | | |
|---|---|---|---|---|
| Source | DF | Sum of Squares | Mean Square | F Ratio 0.3000 |
| Lack Of Fit | 4 | 0.00006000 | 0.000015 | Prob>F |
| Pure Error | 1 | 0.00005000 | 0.000050 | 0.8581 |
| Total Error | 5 | 0.00011000 | | Max RSq |
| | | | | 0.9569 |

| Parameter Estimates | | | | |
|---|---|---|---|---|
| Term | Estimate | Std Error | t Ratio | Prob>\|t\| |
| Intercept | 0.082 | 0.001483 | 55.28 | <.0001* |
| NCS (equivalents)(1.04,1.07) | −0.00625 | 0.001658 | −3.77 | 0.0130* |
| Temperature (C)(13,21) | 0.00625 | 0.001658 | 3.77 | 0.0130* |
| Addition Rate (min.)(30,75) | −0.00375 | 0.001658 | −2.26 | 0.0732 |
| Sulfuric acid (mol%)(0.8,1.2) | −0.00625 | 0.001658 | −3.77 | 0.0130* |

PROCESS FOR MAKING QUINOLONE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a U.S. National Phase Application under 35 U.S.C. §371 of International Patent Application No. PCT/US2009/005276 filed Sep. 23, 2009, which claims the benefit under 35 U.S.C. §119(e) of U.S. Provisional Application No. 61/194,083 filed on Sep. 24, 2008, each of which is hereby incorporated by reference in its entirety.

FIELD OF THE INVENTION

The present invention relates to the field of synthesizing anti-infective compounds. More particularly, the invention relates to synthesizing a family of quinolone compounds useful as anti-infective agents. The invention includes a process for preparing a quinolone compound wherein less than about 0.40% of dimeric impurity of the quinolone is produced.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. Resistant strains of Gram-positive bacteria such as methicillin-resistant staphylocci, penicillin-resistant streptococci, and vancomycin-resistant enterococci have developed, which can cause serious and even fatal results for patients infected with such resistant bacteria. Bacteria that are resistant to macrolide antibiotics, i.e., antibiotics based on a 14- to 16-membered lactone ring, have developed. Also, resistant strains of Gram-negative bacteria such as H. influenzae and M. catarrhalis have been identified. See, e.g., F. D. Lowry, "Antimicrobial Resistance: The Example of Staphylococcus aureus," J. Clin. Invest., 2003, 111(9), 1265-1273; and Gold, H. S, and Moellering, R. C., Jr., "Antimicrobial-Drug Resistance," N. Engl. J. Med., 1996, 335, 1445-53.

Despite the problem of increasing antibiotic resistance, no new major classes of antibiotics have been developed for clinical use since the approval in the United States in 2000 of the oxazolidinone ring-containing antibiotic, N-[[(5S)-3-[3-fluoro-4-(4-morpholinyl)phenyl]-2-oxo-5-oxazolidinyl] methyl acetamide, which is known as linezolid and is sold under the tradename Zyvox® (see compound A). See, R. C. Moellering, Jr., "Linezolid: The First Oxazolidinone Antimicrobial," Annals of Internal Medicine, 2003, 138(2), 135-142.

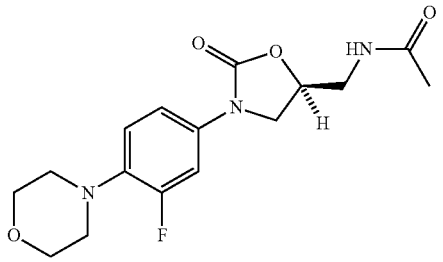

Linezolid was approved for use as an anti-bacterial agent active against Gram-positive organisms. Unfortunately, linezolid-resistant strains of organisms are already being reported. See, Tsiodras et al., Lancet, 2001, 358, 207; Gonzales et al., Lancet, 2001, 357, 1179; Zurenko et al., Proceedings Of The 39$^{th}$ Annual Interscience Conference On Antibacterial Agents And Chemotherapy (ICAAC); San Francisco, Calif., USA, (Sep. 26-29, 1999).

Notwithstanding the foregoing, there is an ongoing need for new anti-infective agents and for methods of making them.

BRIEF DESCRIPTION OF THE FIGURES

FIG. 4 shows an initial design of experiments experimental table.

FIG. 5d shows parameter estimates for the initial design of experiments of FIG. 4.

FIG. 5e show a residual by predicted plot for the initial design of experiments of FIG. 4.

FIG. 5f shows sorted parameter estimates for the initial design of experiments of FIG. 4.

FIG. 7 shows a robustness design of experiments experimental table for a second design of experiments.

SUMMARY OF THE INVENTION

Figure 1:
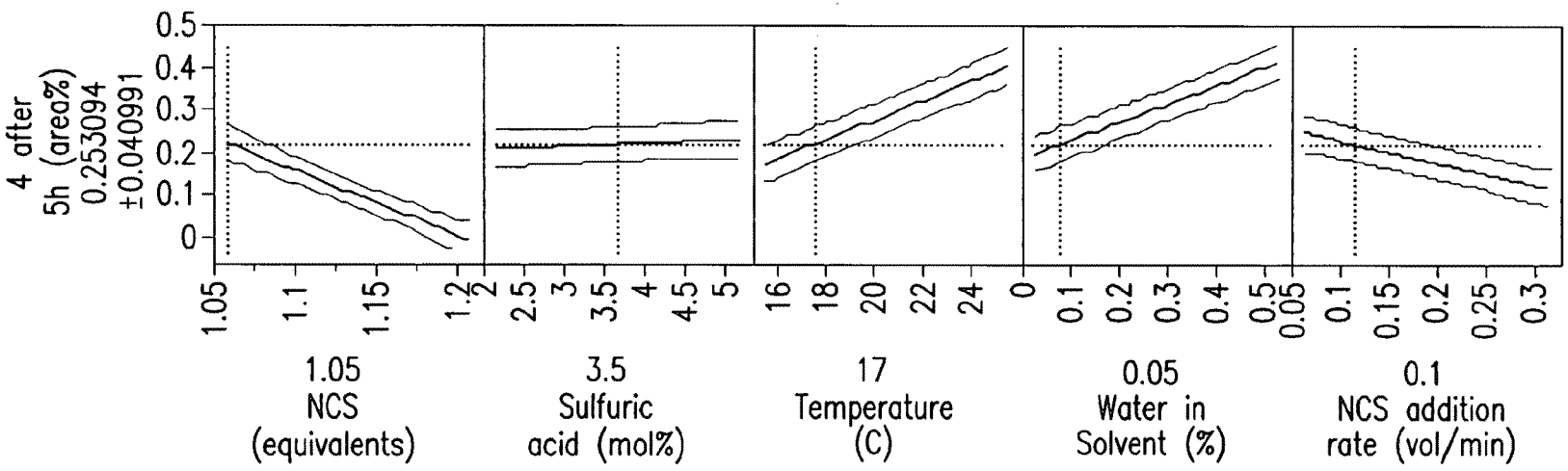
FIG. 1 shows a prediction profiler for the amount of dimeric impurity 4 when ethyl acetate (EtOAc) is the solvent. This was based on the initial design of experiments. The center line of each plot shows the predicted values and the two lines flanking the center line represent the approximately ±95 percent confidence levels. The horizontal dotted line signifies a dimer 4 level of 0.235094 percent. The vertical dotted lines signify the variables for 1.05 equivalents of N-chlorosuccinimide (NCS), 3.5 mole percent sulfuric acid, 17° C., 0.05 percent water content in the solvent and an NCS addition rate of 0.1 volume per minute. The 95 percent confidence limit is ±0.040991 for the values indicated in the preceding sentence.

The present invention relates to the field of synthesizing anti-infective compounds. More particularly, the invention relates to synthesizing a family of quinolone compounds useful as anti-infective agents.

The present invention relates to a process for preparing a quinolone compound comprising the step of reacting a des-chloro quinolone compound or a pharmaceutically acceptable salt or ester thereof with a chlorinating agent and an acid, wherein less than about 0.40% on an area percent basis as quantified by analytical HPLC of dimeric impurity of the quinolone is produced.

In other embodiments the present invention relates to a process where the des-chloro quinolone compound is 1-(6-amino-3,5-difluoropyridin-2-yl)-6-fluoro-7-(3-hydroxy-azetidin-1-yl)-4-oxo-1,4-dihydroquinoline-3-carboxylic acid or a pharmaceutically acceptable salt or ester thereof, the quinolone compound is 1-(6-amino-3,5-difluoropyridin-2-yl)-8-chloro-6-fluoro-7-(3-hydroxy-azetidin-1-yl)-4-oxo-1,4-dihydroquinoline-3-carboxylic acid or a pharmaceutically acceptable salt or ester thereof.

In other embodiments the present invention relates to a process where the dimeric impurity is compound 1-amino-3-(azetidin-3-yloxy)-propan-2-ol-bis(N,N'-quinolone carboxylic acid), or a pharmaceutically acceptable salt or ester thereof. In other embodiments the present invention relates to a process where the dimeric impurity is a mono-ester. In other embodiments the present invention relates to a process where the dimeric impurity is a di-ester.

In other embodiments the present invention relates to a process where the chlorinating agent is N-chlorosuccinimide.

In other embodiments the present invention relates to a process where the acid is selected from the group consisting of sulfuric acid, hydrochloric acid, hydrobromic acid, phosphoric acid, trifluoroacetic acid, triflic acid, methanesulfonic acid, p-toluenesulfonic acid or perchloric acid, and mixtures thereof.

In other embodiments the present invention relates to a process where the acid is sulfuric acid.

In other embodiments the present invention relates to a process where the reaction is run at a temperature from about 0° C. to about 30° C.

In other embodiments the present invention relates to a process where the reaction is run at a temperature from about 15° C. to about 25° C.

In other embodiments the present invention relates to a process where the reaction is run at a temperature from about 13° C. to about 21° C.

In other embodiments the present invention relates to a process where the molar ratio of N-chlorosuccinimide to des-chloro quinolone is greater than about 1.

In other embodiments the present invention relates to a process where the molar ratio of N-chlorosuccinimide to des-chloro quinolone is from about 1.05 to 1.2.

In other embodiments the present invention relates to a process where the molar ratio of N-chlorosuccinimide to des-chloro quinolone is from about 1.04 about 1.07.

In other embodiments the present invention relates to a process where the molar ratio of sulfuric acid to des-chloro quinolone is from about 0.005 to about 0.05.

In other embodiments the present invention relates to a process where the molar ratio of sulfuric acid to des-chloro quinolone is from about 0.007 to about 0.02.

In other embodiments the present invention relates to a process where the molar ratio of sulfuric acid to des-chloro quinolone is from about 0.008 to about 0.012.

In other embodiments the present invention relates to a process where an acetate ester as a solvent.

In other embodiments the present invention relates to a process where the acetate ester is selected from the group consisting of methyl acetate, ethyl acetate, and mixtures thereof.

In other embodiments the present invention relates to a process where said acetate ester is methyl acetate.

In other embodiments the present invention relates to a process comprising the further step of reacting the quinolone compound with a base.

In other embodiments the present invention relates to a process where the base is a hydroxide base.

In other embodiments the present invention relates to a process where the hydroxide base is selected from the group consisting of sodium hydroxide, potassium hydroxide, lithium hydroxide, barium hydroxide, and mixtures thereof.

In other embodiments the present invention relates to a process where the hydroxide base is potassium hydroxide.

In other embodiments the present invention relates to a process using a mixture of C1-C6 alcohol and water as a solvent.

In other embodiments the present invention relates to a process where the C1-C6 alcohol is isopropanol.

In other embodiments the present invention relates to a process where the process is a commercial scale process.

In other embodiments the present invention relates to a composition comprising a quinolone compound or salt or ester thereof having less than about 0.40% of dimeric impurity of the quinolone compound.

In other embodiments the present invention relates to a composition wherein the quinolone compound is 1-(6-amino-3,5-difluoropyridin-2-yl)-8-chloro-6-fluoro-7-(3-hydroxy-azetidin-1-yl)-4-oxo-1,4-dihydroquinoline-3-carboxylic acid or a pharmaceutically acceptable salt or ester thereof.

In other embodiments the present invention relates to a composition where the dimeric impurity is 1-amino-3-(azetidin-3-yloxy)-propan-2-ol-bis(N,N '-quinolone carboxylic acid), or a pharmaceutically acceptable salt or ester thereof.

In other embodiments the present invention relates to a composition where the composition is a commercial scale composition.

In other embodiments the present invention relates to a process or a composition wherein the dimeric impurity is less than about 0.35%.

In other embodiments the present invention relates to a process or a composition wherein the dimeric impurity is less than about 0.30%.

In other embodiments the present invention relates to a process or a composition wherein the dimeric impurity is less than about 0.25%.

In other embodiments the present invention relates to a process or a composition wherein the dimeric impurity is less than about 0.20%.

In other embodiments the present invention relates to a process or a composition wherein the dimeric impurity is less than about 0.15%.

In other embodiments the present invention relates to a process or a composition wherein the dimeric impurity is less than about 0.10%.

In other embodiments the present invention relates to a process or a composition wherein the dimeric impurity is less than about 0.05%.

In other embodiments the present invention relates to a process or a composition wherein the dimeric impurity is less than about 0.04%.

In other embodiments the present invention relates to a process or composition where the dimeric impurity is less than about 0.03%.

In other embodiments the present invention relates to a process or composition where the dimeric impurity is less than about 0.02%.

In other embodiments the present invention relates to a process or composition where said dimeric impurity is less than about 0.01%.

DETAILED DESCRIPTION OF THE INVENTION

Quinolones

The processes and compositions of the present invention comprise a quinolone compound.

Quinolone compounds, such as pyridonecarboxylic acid derivatives, useful herein are described, including their synthesis, formulation, and use, in U.S. Pat. No. 6,156,903, to Yazaki et al., issued Dec. 5, 2000 and its certificates of correction of Nov. 13, 2001 and Dec. 11, 2001; U.S. Pat. No. 6,133,284, to Yazaki et al., issued Oct. 17, 2000; U.S. Pat. No. 5,998,436, to Yazaki et al., issued Dec. 7, 1999 and its certificates of correction of Jan. 23, 2001, Oct. 30, 2001, and Dec. 17, 2002; PCT Application No. WO 2006/110815, to Abbott Laboratories, published Oct. 19, 2006; PCT Application No. WO 2006/042034, to Abbott Laboratories, published Apr. 20, 2006, PCT Application No. WO 2006/015194, to Abbott Laboratories, published Feb. 9, 2006; PCT Application No. WO 01/34595, to Wakunaga Pharmaceutical Co., Ltd., published May 17, 2001; and PCT Application No. WO 97/11068, to Wakunaga Pharmaceutical Co., Ltd., published Mar. 27, 1997.

Pyridonecarboxylic acid derivatives of the present invention include compounds corresponding to the following structure (Pyridonecarboxylic Acid Derivative 1)

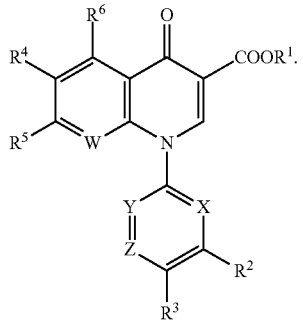

Pyridonecarboxylic Acid Derivative 1 wherein $R^1$ represents a hydrogen atom or a carboxyl protective group; $R^2$ represents a hydroxyl group, a lower alkoxy group, or a substituted or unsubstituted amino group; $R^3$ represents a hydrogen atom or a halogen atom; $R^4$ represents a hydrogen atom or a halogen atom; $R^5$ represents a halogen atom or an optionally substituted saturated cyclic amino group; $R^6$ represents a hydrogen atom, a halogen atom, a nitro group, or an optionally protected amino group; X, Y and Z may be the same or different and respectively represent a nitrogen atom, CH or $CR^7$ (wherein $R^7$ represents a lower alkyl group, a halogen atom, or a cyano group), with the proviso that at least one of X, Y and Z represent a nitrogen atom, and W represents a nitrogen atom or $CR^8$ (wherein $R^8$ represents a hydrogen atom, a halogen atom, or a lower alkyl group), and with the proviso that when $R^1$ represents a hydrogen atom, $R^2$ represents an amino group, $R^3$ and $R^4$ represent a fluorine atom, $R^6$ represents a hydrogen atom, X represents a nitrogen atom, Y represents $CR^7$ (wherein $R^7$ represents a fluorine atom), Z represents CH, and W is $CR^8$ (wherein $R^8$ represents a chlorine atom), then $R^5$ is not a 3-hydroxyazetidine-1-yl group; or a pharmaceutically acceptable salt, ester, or prodrug thereof.

As described in the foregoing paragraph, when $R^1$ is a carboxyl protective group, it may be any carboxylate ester residue which cleaves relatively easily to generate the corresponding free carboxyl group. Exemplary carboxyl protective groups include those which may be eliminated by hydrolysis, catalytic reduction, and other treatments under mild conditions such as lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group; and aryl groups such as phenyl group and naphthyl group; and those which may be readily eliminated in the body such as lower alkanoyloxy lower alkyl groups such as acetoxymethyl group and pivaloyloxymethyl group; lower alkoxycarbonyloxy lower alkyl group such as methoxycarbonyloxymethyl group and 1-ethoxycarbonyloxyethyl group; lower alkoxymethyl group such as methoxymethyl group; lactonyl group such as phthalidyl; di-lower alkylamino lower alkyl group such as 1-dimethylaminoethyl group; and (5-methyl-2-oxo-1,3-dioxole-4-yl)methyl group.

It is noted that the substituents $R^1$, $R^2$, $R^3$, $R^4$, $R^5$, $R^6$, $R^7$, $R^8$, $R^9$, A, $J^1$, $J^2$, $J^3$, W, X, Y, Z, e, f, and g are defined herein for convenience with respect to the chemical structure for the pyridonecarboxylic acid derivatives.

In other embodiments, the present invention relates to a process for preparing a pyridonecarboxylic acid derivative of structure Pyridonecarboxylic Acid Derivative 1, wherein W is $CR^8$, wherein $R^8$ represents a hydrogen atom, a halogen atom, or a lower alkyl group.

In other embodiments, the present invention relates to a process for preparing a pyridonecarboxylic acid derivative of structure Pyridonecarboxylic Acid Derivative 1, wherein $R^5$ is a group represented by the following formula (a) or (b):

(a)

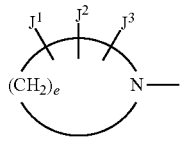

(b)

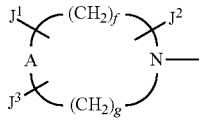

wherein A represents an oxygen atom, sulfur atom or $NR^9$ (wherein $R^9$ represents hydrogen atom or a lower alkyl group), e represents a number from 3 to 5, f represents a number from 1 to 3, g represents a number from 0 to 2, $J^1$, $J^2$ and $J^3$, which may be the same or different from one another, represent a hydrogen atom, hydroxyl group, lower alkyl group, amino lower alkyl group, amino group, lower alkylamino group, lower alkoxy group, or a halogen atom.

In other embodiments, the present invention relates to a process for preparing a pyridonecarboxylic acid derivative of structure Pyridonecarboxylic Acid Derivative 1, wherein $R^5$ is a group represented by formula (a).

(a)

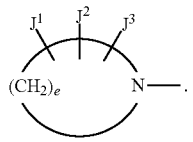

In other embodiments, the present invention relates to a process for preparing a pyridonecarboxylic acid derivative of structure Pyridonecarboxylic Acid Derivative 1, wherein e in the formula (a) is 3 or 4.

(a)

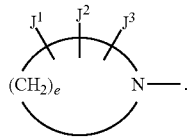

In other embodiments, the present invention relates to a process for preparing a pyridonecarboxylic acid derivative of structure Pyridonecarboxylic Acid Derivative 1, wherein $R^1$ is a hydrogen atom; $R^2$ is an amino group, lower alkylamino group, or a di-lower alkylamino group; $R^3$ is a halogen atom; $R^4$ is a halogen atom; $R^6$ is hydrogen atom; X is a nitrogen atom; Y and Z are CH or $CR^7$ (wherein $R^7$ is a lower alkyl group or a halogen atom); and W is $CR^8$ (wherein $R^8$ is a halogen atom or a lower alkyl group).

In other embodiments, the present invention relates to a process for preparing a pyridonecarboxylic acid derivative of structure Pyridonecarboxylic Acid Derivative 1, wherein $R^2$ is amino group; $R^3$ is fluorine atom; $R^4$ is a fluorine atom; Y is CF; Z is CH; W is $CR^8$ (wherein $R^8$ is a chlorine atom, bromine atom or a methyl group), and e in formula (a) is 3.

(a)

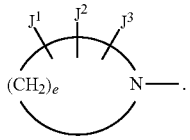

In other embodiments, the present invention relates to a process for preparing a pyridonecarboxylic acid, wherein said pyridonecarboxylic acid corresponds to the following structure:

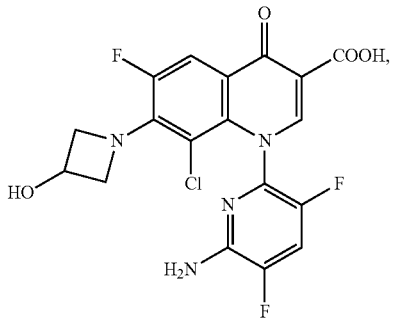

or a pharmaceutically acceptable salt, ester, or prodrug thereof. This foregoing pyridonecarboxylic acid is also known by the publicly disclosed code names Abbott Laboratories ABT-492, Wakunaga Pharmaceutical Co., Ltd. WQ 3034, Rib-X Pharmaceuticals, Inc., RX-3341, the USAN delafloxacin, and also by the chemical names 1-(6-amino-3,5-difluoro-2-pyridinyl)-8-chloro-6-fluoro-1,4-dihydro-7-(3-hydroxy-1-azetidinyl)-4-oxo-3-quinolinecarboxylic acid, 1-(6-amino-3,5-difluoro-2-pyridinyl)-8-chloro-6-fluoro-1,4-dihydro-7-(3-hydroxyazetidin-1-yl)-4-oxo-3-quinolinecarboxylic acid, 3-quinolinecarboxylic acid, 1-(6-amino-3,5-difluoro-2-pyridinyl)-8-chloro-6-fluoro-1,4-dihydro-7-(3-hydroxy-1-azetidinyl)-4-oxo, and 1-(6-amino-3,5-difluoropyridin-2-yl)-8-chloro-6-fluoro-7-(3-hydroxyazetidin-1-yl)-4-oxo-1,4-dihydroquinoline-3-carboxylic acid. This carboxylic acid form of the compound corresponds to the CAS registry number 189279-58-1. Furthermore, WO 2006/042034, cited above discloses the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt)] and the trihydrate of the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt)]. The D-glucitol salt and the D-glucitol salt trihydrate correspond to the CAS registry numbers 352458-37-8 and 883105-02-0, respectively. D-glucitol corresponds to the CAS registry number 6284-40-8. WO 2006/042034 also discloses a crystalline form of the D-glucitol salt characterized when measured at about 25° C. with Cu-Ka radiation, by the powder diffraction pattern shown in FIG. 1 (see WO 2006/042034) and a crystalline form of the D-glucitol salt trihydrate when measured at about 25° C. with Cu-Ka radiation, by the powder diffraction pattern shown in FIG. 2 (see WO 2006/042034). These D-glucitol salts are useful in the present invention. Also, see A. R. Haight et al., "Synthesis of the Quinolone ABT-492: Crystallizations for Optimal Processing", Organic Process Research & Development (2006), 10(4), 751-756.

The terms "commercial scale process" and "commercial scale composition" refer to a process and composition, respectively, which is run or produced as a single batch of at least about 100 grams.

Identification and Suppression of a Dimer Impurity in the Development of Delafloxacin See, Hanselmann, R., et al., "Identification and Suppression of a Dimer Impurity in the Development of Delafloxacin", Organic Process Research & Development, vol. 13, pages 54-59 (2009).

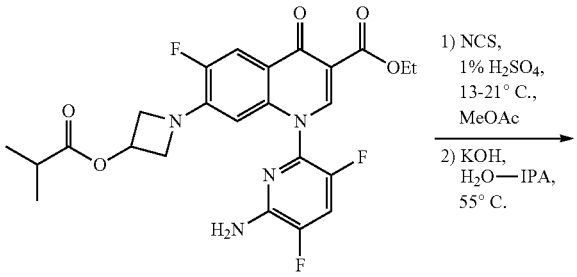

1

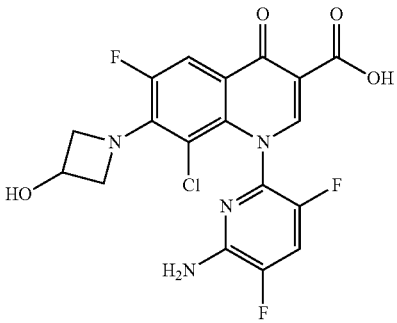

3

Delafloxacin is a 6-fluoroquinolone antibiotic which is under development at Rib-X Pharmaceuticals, Inc. During initial scale up runs to prepare delafloxacin, up to 0.43% of a new impurity arose in the penultimate chlorination step. This was identified as a dimeric adduct of delafloxacin. Subsequent application of design of experiments (DoE's) led to the identification of the factors responsible for this impurity. Implementation of the knowledge gained from the DoE's reproducibly enabled the suppression of this impurity to acceptable levels.

Antimicrobial resistance in the community and hospital settings has been a growing public health concern due to the continuing emergence of multidrug resistant bacterial strains. See (a) Cosgrove, S. E.; Carmeli, Y. Clin. Infect. Dis. 2003, 36, 1433. (b) Seybold, U.; Kourbatova, E. V.; Johnson, J. G.; Halvosa, S. J.; Wang, Y. F.; King, M. D.; Ray, S. M.; Blumberg, H. M. Clin. Infect. Dis. 2006, 42, 647. and (c) Tenover, F. C.; McDougal, L. K.; Goering, R. V.; Kiligore, G.; Projan, S. J.; Patel, J. B.; Dunman, P. M. J. Clin. Microbiol. 2006, 44, 108.

Methicillin-resistant Staphylococcus aureus (MRSA) ranks as the most frequently isolated pathogen in hospital intensive care units in the United States and the incidence of MRSA occurrence increased from 35.9% in 1992 to 64.4% in 2003. See Klevens, R. M.; Edwards, J. R.; Tenover, F. C.; McDonald, L. C.; Horan, T.; Gaynes, R. Clin. Infect. Dis. 2006, 42, 389.

Since the introduction of nalidixic acid nearly 40 years ago, quinolone antibiotics have occupied a prominent place in the array of antibiotics. 6-Fluoroquinolones such as ciprofloxacin have especially gained an expanding role in the treatment of infections, due to their broad spectrum of application. See (a) Bush, K. Clin. Microbiol. Infect. 2004, 10 (Suppl. 4), 10. and (b) Emmerson, A. M.; Jones, A. M. J. Antimicrob. Chemother. 2003, 51 (Suppl. S1), 13.

Delafloxacin is a 6-fluoroquinolone antibiotic with excellent antibacterial activity against gram-positive organisms, including both methicillin-susceptible S aureus and MRSA. It is currently undergoing phase II clinical trials. Delafloxacin was initially developed by Wakunaga Pharmaceuticals and Abbott Laboratories and was subsequently licensed by Rib-X Pharmaceuticals, Inc.

The synthesis of delafloxacin initially underwent development by Abbott Laboratories (Scheme 1) and a key step in this is a selective chlorination on the 8-position of the functionalized quinolone 1 (the des-chloro quinolone). See, (a) Haight, A. R.; Ariman, S. Z.; Barnes, D. M.; Benz, N. J.; Gueffier, F. X.; Henry, R. F.; Hsu, M. C.; Lee, E. C.; Morin, L.; Pearl, K. B.; Peterson, M. J.; Plata, D. J.; Willcox, D. R. Org. Process Res. Dev. 2006, 4, 751. and (b) Barnes, D. M.; Christesen, A. C.; Engstrom, K. M.; Haight, A. R.; Hsu, M. C.; Lee, E. C.; Peterson, M. J.; Plata, D. J.; Raje, P. S.; Stoner, E. J.; Tedrow, J. S.; Wagaw, S. Org. Process Res. Dev. 2006, 4, 803.

In this process a solution of 1 in a mixture of methyl acetate (MeOAc) and ethyl acetate is chlorinated using NCS in the presence of 3.5 mole % of H2SO4, affording 2. This is followed by solvent exchange and saponification with KOH to yield 3. Delafloxacin is obtained after salt formation with N-methyl-D-glucamine.

Scheme 1: Synthesis of delafloxacin

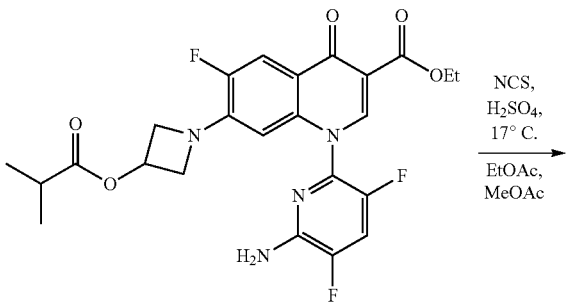

1

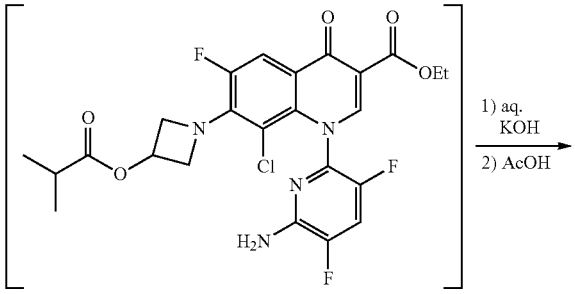

2

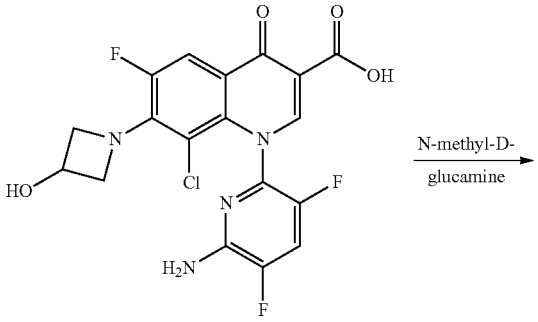

3

-continued

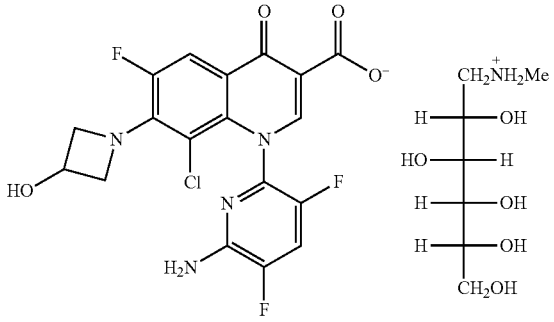

Delafloxacin

Despite initial success in implementing this process, we encountered difficulties upon scale up of this step in that up to 0.43 area % of a new impurity was detected by HPLC at RRT 1.60 after isolation of 3. Additionally, this new impurity turned out to be difficult to purge during the final salt formation. Thus, we decided to initiate a study to identify this impurity, understand how it was being formed and suppress its generation.

Results and Discussion

Despite numerous attempts to isolate this new impurity by preparative HPLC, we were unable to do so and only the molecular weight was established by HPLC-MS as 880 Da. The measured molecular weight of this impurity is exactly double of the acid 3, which suggested a dimeric derivative of this compound. Close examination of the purity profile of the substrate of the chlorination reaction did not lead to the detection of any impurity that could similarly be assigned a dimeric structure and its formation was therefore attributed to the chlorination—hydrolysis sequence. A number of potential dimeric adducts that could arise in this step were considered, including 4, which would result from cleavage of the azetidine moiety in one unit of 3 and reacting with the hydroxyl group of a second. In order to investigate this possibility further, we embarked on the synthesis of 4.

Scheme 2: Retrosynthesis of purported impurity 4

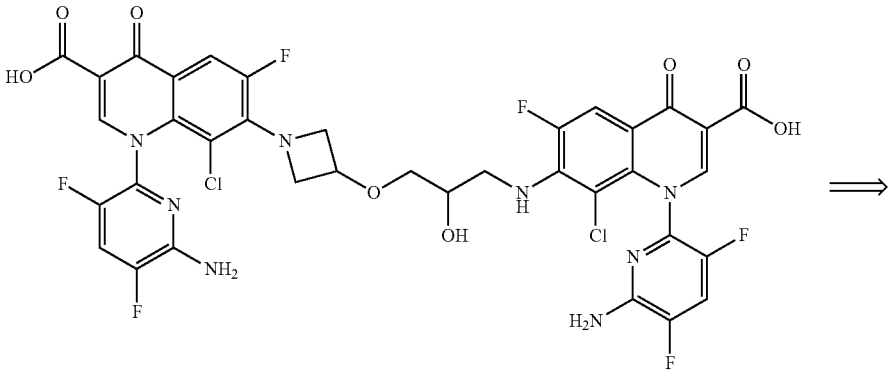

-continued

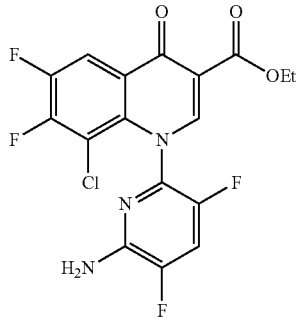

6

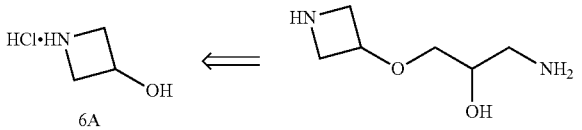

6A 5

Retrosynthetically (Scheme 2), molecule 4 is readily disconnected into a suitably protected amino alcohol 5 and quinolone 6; the latter is a known compound. Fragment 5 can be prepared from commercially available azetidin-3-ol hydrochloride 7. See, (a) Yazaki, A.; Niino, Y; Ohshita, Y.; Hirao, Y.; Amano, H.; Hayashi, N.; Kuramoto, Y. PCT Int. Appl. WO 9711068, 1997. CAN: 126, 305587. and (b) Yazaki, A.; Aoki, S. PCT Int. Appl. WO 2001034595, 2001. CAN: 134, 366811.

The synthesis thus commenced from 7, in which the nitrogen was protected as a benzyl carbamate to yield 8 in quantitative yield. This adduct was alkylated with racemic epichlorohydrin to give 9 in 84% yield. Epoxide opening of 9 with ammonia gave 10, which was condensed without purification with 6 to yield 11 in 83% overall yield. Deprotection of the Cbz group under hydrogenation conditions gave 12 in 93% yield. A second condensation with 6 resulted in formation of the dimeric compound 13 in 71% yield. After saponification the presumed impurity 4 was obtained in 98% yield.

Scheme 3: Synthesis of impurity 4

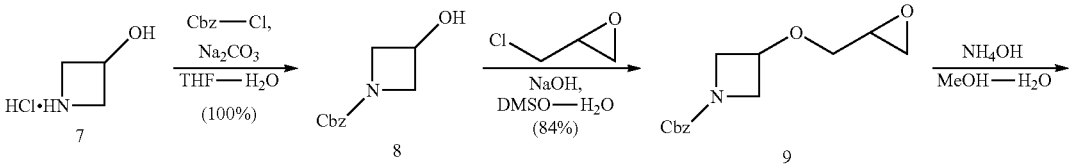

7 8 9

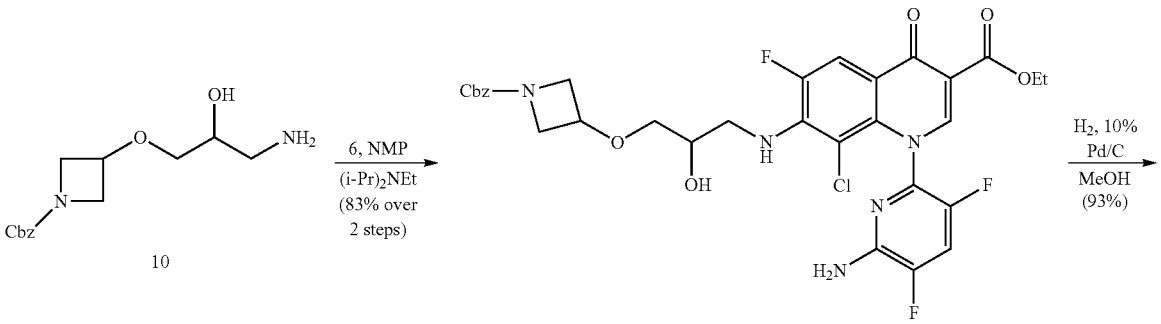

10 11

-continued

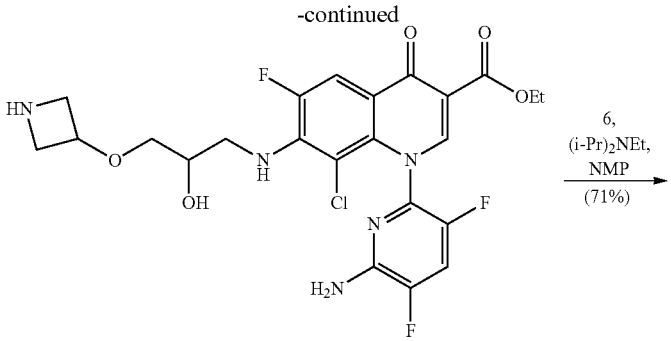

12

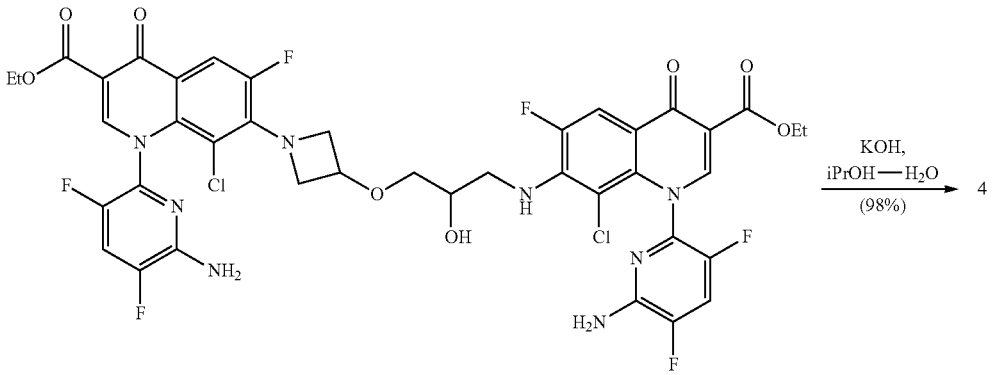

13

With synthetic 4 at hand, the unknown impurity in a contaminated batch of delafloxacin was compared with synthesized 4 via spiking experiments and comparison by HPLC-MS and HPLC-UV. To our delight, synthetic 4 matched unambiguously with the unknown impurity seen in previously manufactured batches of delafloxacin.

In order to understand the dynamics of the formation of impurity 4, we decided to investigate the chlorination reaction further in a design of experiments (DoE) study. The following factors were chosen to be investigated in a DoE study of resolution IV, over ranges as specified: temperature (15-25° C.), amount of NCS (1.05-1.2 eq.), amount of H2SO4 (2-5 mol %), water content in solvent (0-0.5%), solvent volume (2-3 vol.), solvent (methyl acetate/ethyl acetate) and NCS addition rate (0.05-0.3 vol/min.). See, FIG. 4, FIGS. 5a, 5b, 5c, 5d, 5e, and 5f, FIGS. 6a and 6b, FIG. 7, and FIGS. 8a, 8b, 8c, 8d, 8e, 8f, and 8g. A total of 19 chlorination reactions were performed in a MultiMax™ reactor, available from Mettler-Toledo, Inc., 1900 Polaris Parkway, Columbus, Ohio, 43240.

In each case samples from the reactions were quenched after 5 h, saponified with KOH and the crude reaction mixtures were analyzed by HPLC. In order to determine the amount of 4, the chlorinated samples 2 were saponified to 3. The area % value for impurity 4 that resulted in each case was processed and analyzed using the DoE software. The experimental design and analysis were conducted using JMP, Design of Experiments, Version 7, SAS Institute Inc., Cary, N.C., 1989-2007, using a stepwise fit followed by a standard least squares method.

An excellent correlation of R2 of 0.997 was obtained following processing of the data. Of the main effects, higher amounts of NCS, lowering the temperature and faster addition of the NCS solution as well as use of dry solvents had the most beneficial impact on suppressing the amount of impurity 4 (FIG. 1). Methyl acetate containing less than 500 ppm water was used, prior to adjustment as required by the appropriate experiment in the DoE's. Additionally, a strong interaction was observed between the amount of NCS and solvent, in that methyl acetate is preferred when only a slight excess of NCS is used. In order to suppress any overchlorination of 2, 1.05 equivalents of NCS is preferred and hence methyl acetate was chosen as the solvent of choice for this step. A more detailed analysis can be found in FIG. 4, FIGS. 5a, 5b, 5c, 5d, 5e, and 5f, FIGS. 6a and 6b, FIG. 7, and FIGS. 8a, 8b, 8c, 8d, 8e, 8f, and 8g.

From a mechanistic point of view, we postulate that impurity 4 could arise from an initial acid catalyzed activation of the azetidine ring which triggers an isobutyric ester/chloride induced ring opening sequence to 16. During the subsequent saponification 16 reacts with the hydrolysis intermediate 17 or 3 to 4 (Scheme 4). Saponification and subsequent epoxide formation of 16 prior to condensation with 3 or 17 cannot be ruled out. The validity of this sequence was further strengthened by a subsequent HPLC-MS analysis of a crude chlorination reaction before saponification. In this, an impurity with a molecular weight of 574 Da, which matches 16, was detected in approximate equal amounts compared to 4 after saponification.

Scheme 4: Proposed mechanism of impurity 4

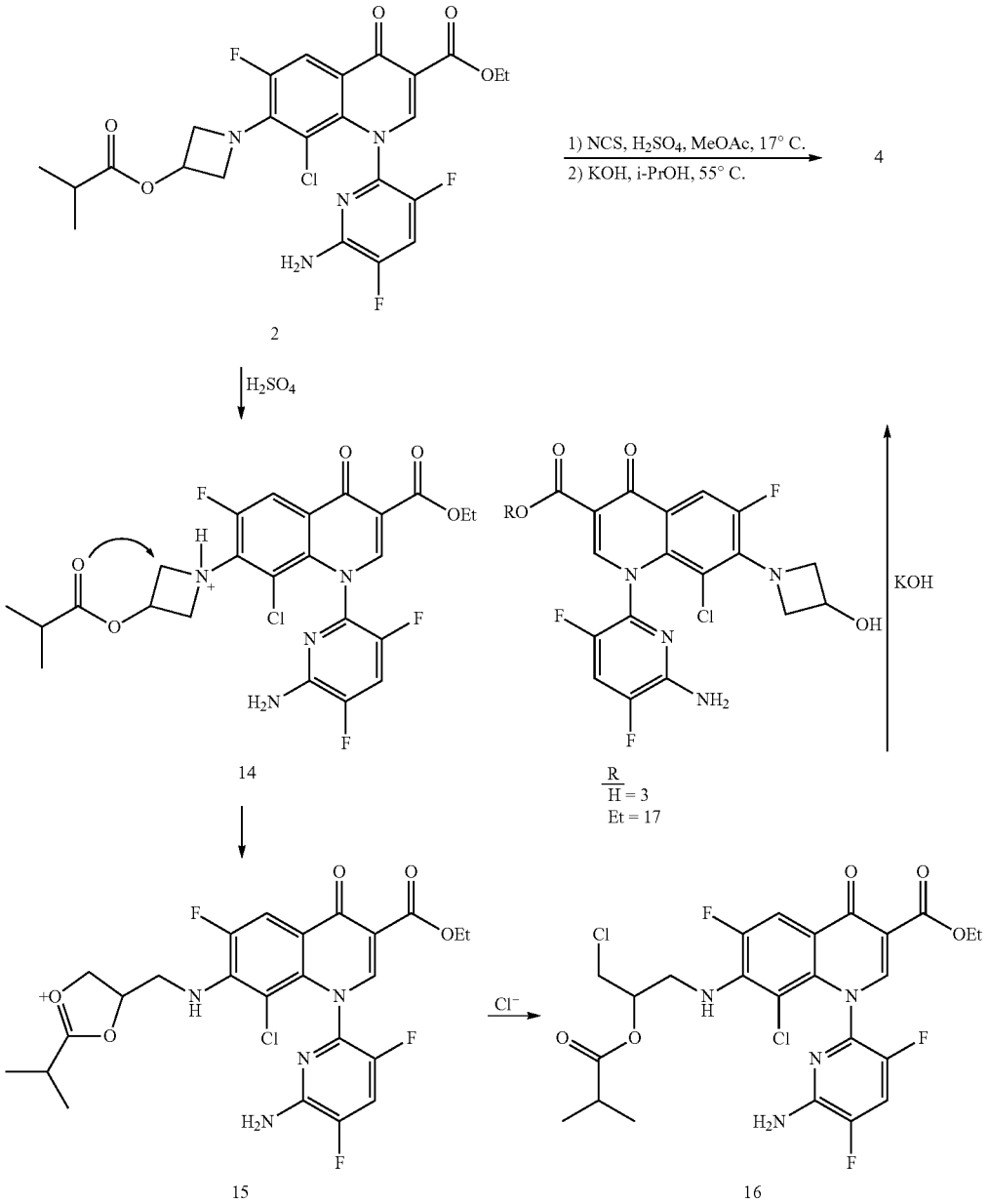

Figure 2:
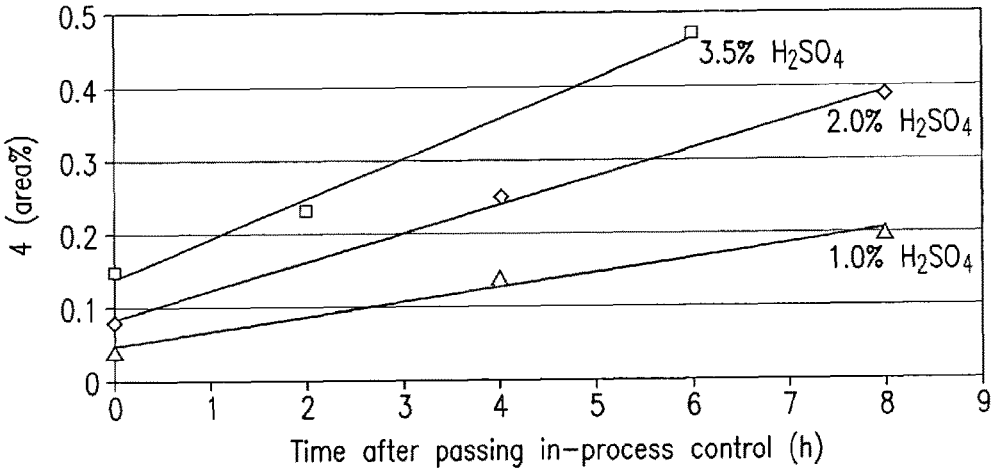
FIG. 2 shows the impact of $H_2SO_4$ and time on the levels of dimeric impurity 4.

Based on this hypothetical mechanism, a time dependency for the formation of 4 during the chlorination process cannot be excluded, and since the reaction time was kept constant in the DoE study, it was decided to evaluate this parameter independently. A chlorination reaction was performed using 3.5% of $H_2SO_4$ and methyl acetate as solvent at 15° C. and a sample was quenched after the reaction was deemed to be complete. Additional samples were quenched after 2 h and 6 h, saponified and analyzed by HPLC. Not surprisingly, a steady increase of the impurity 4 over time was seen. This result has an impact on controlling the chlorination process, in that an adequate turn around time for the HPLC monitoring of this reaction would be necessary in order to minimize the formation of 4. However, subsequent experiments showed that decreasing the amount of $H_2SO_4$ to 1% diminished the amount of impurity 4 produced over time without having a significant impact on the chlorination reaction time or the quality of 3 (FIG. 2). Thus, an acceptable turn around time for the in-process control can be achieved when a level of 1% of $H_2SO_4$ is employed as catalyst.

Figure 3:
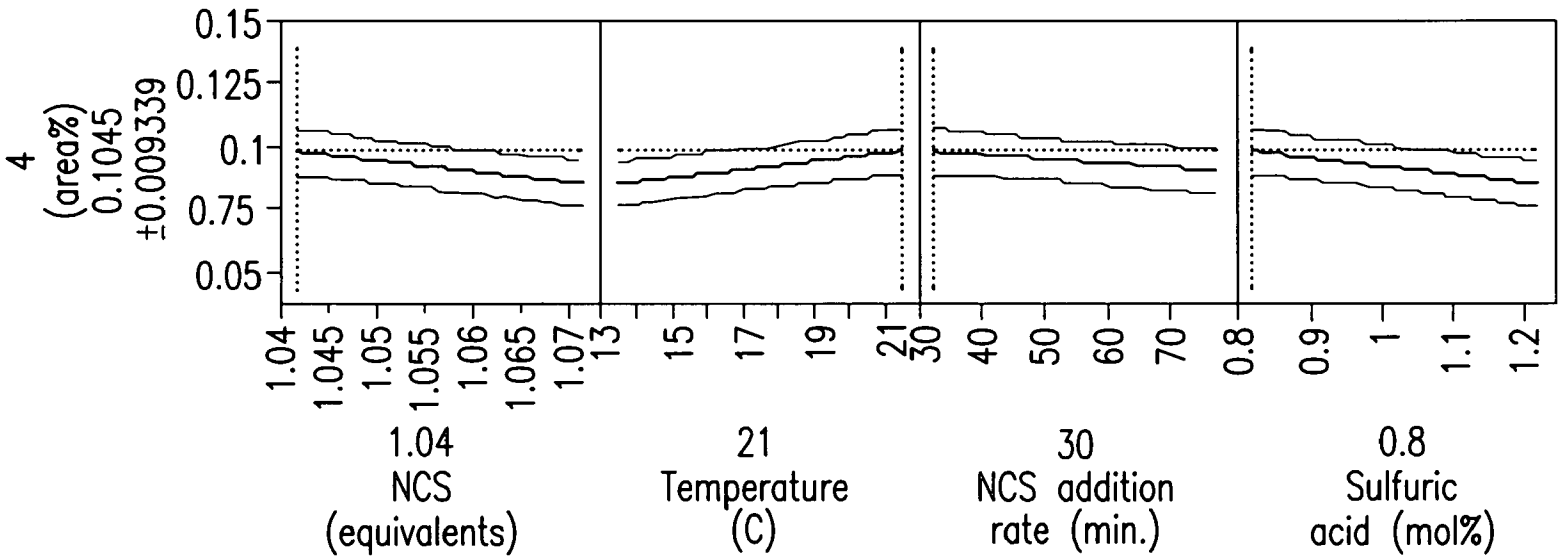
FIG. 3 shows the worst case scenario in prediction profiler for the amount of dimeric impurity 4 for robustness of DoE, i.e. for the second design of experiments. The center line of each plot shows the predicted values and the two lines flanking the center line represent the approximately ±95 percent confidence levels. The horizontal dotted line signfies a dimer 4 level of 0.1045 percent. The vertical dotted lines signify the variables for 1.04 equivalents of N-chlorosuccinicmide (NCS), 21° C., an NCS addition rate of 30 minutes, and 0.8 mole percent sulfuric acid. The 95 percent confidence limit is +0.009339 for the values indicated in the preceding sentence.
Figures 5A, 5B, 5C:
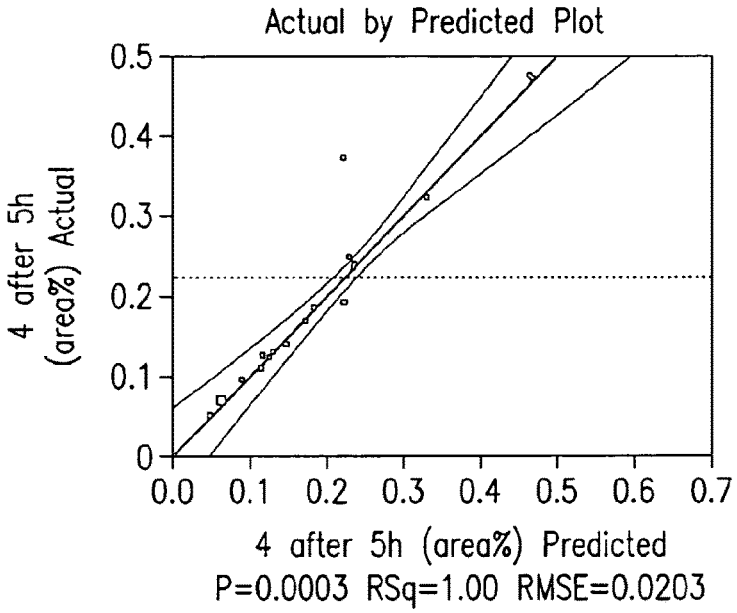
FIG. 5a shows an actual by prediction plot for the initial design of experiments of FIG. 4.
FIG. 5b shows a summary of fit for the initial design of experiments of FIG. 4.
FIG. 5c shows an analysis of variance for the initial design of experiments of FIG. 4.
Figure 6A:
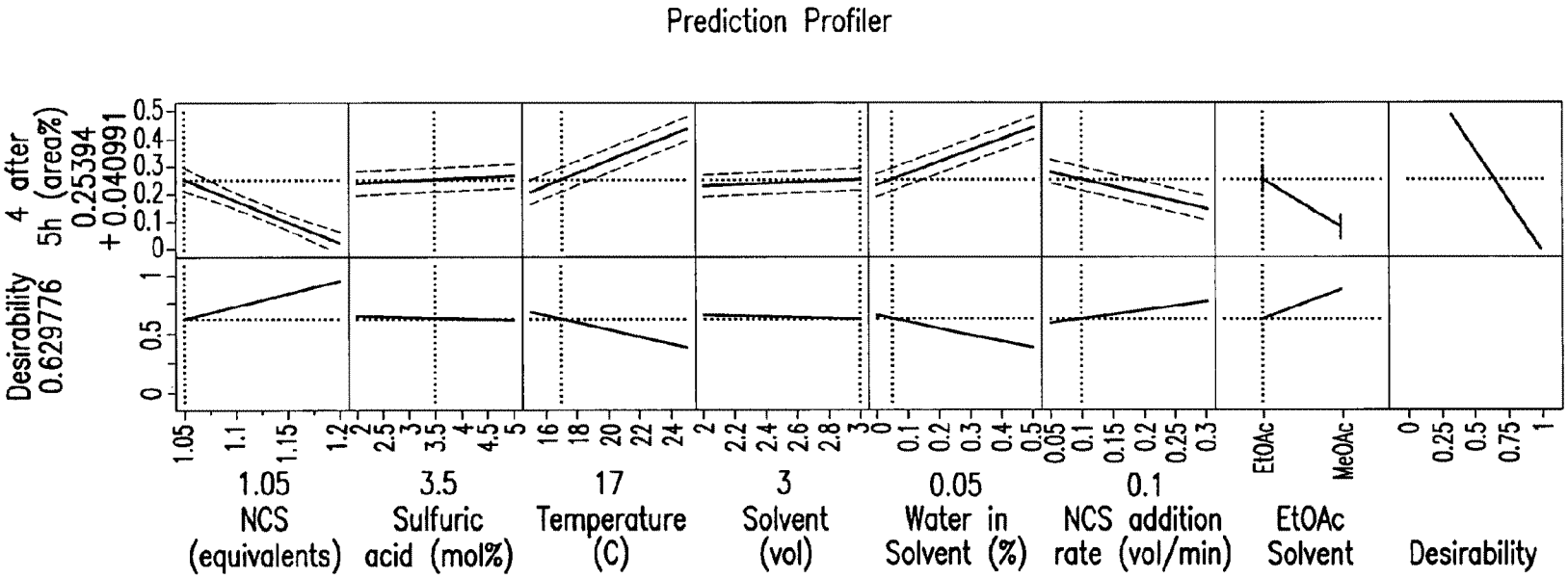
FIG. 6a shows a prediction profiler for the initial design of experiments of FIG. 4.
Figure 6B:
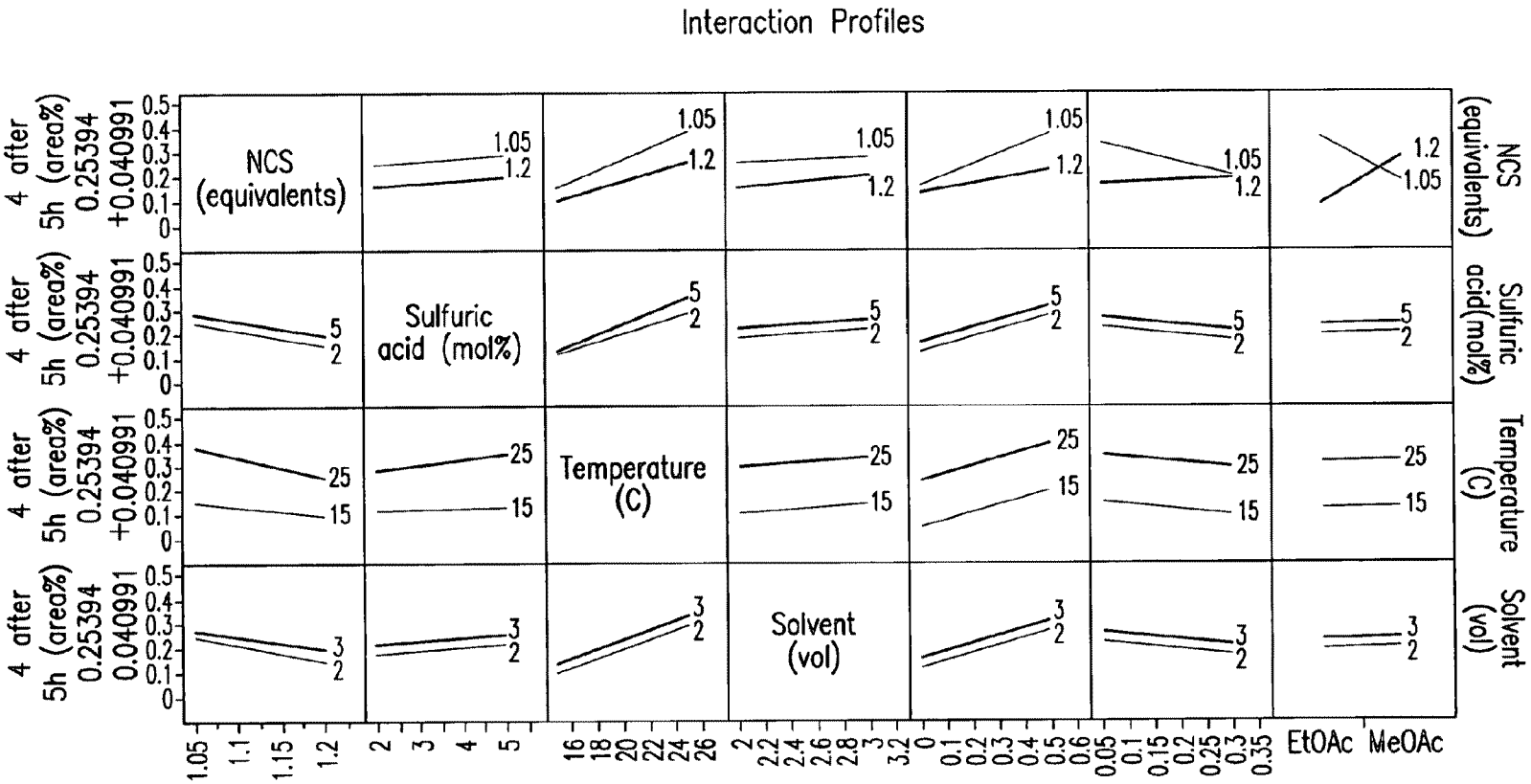
FIG. 6b show interaction profiles for the initial design of experiments of FIG. 4.
Figures 1, 6B:
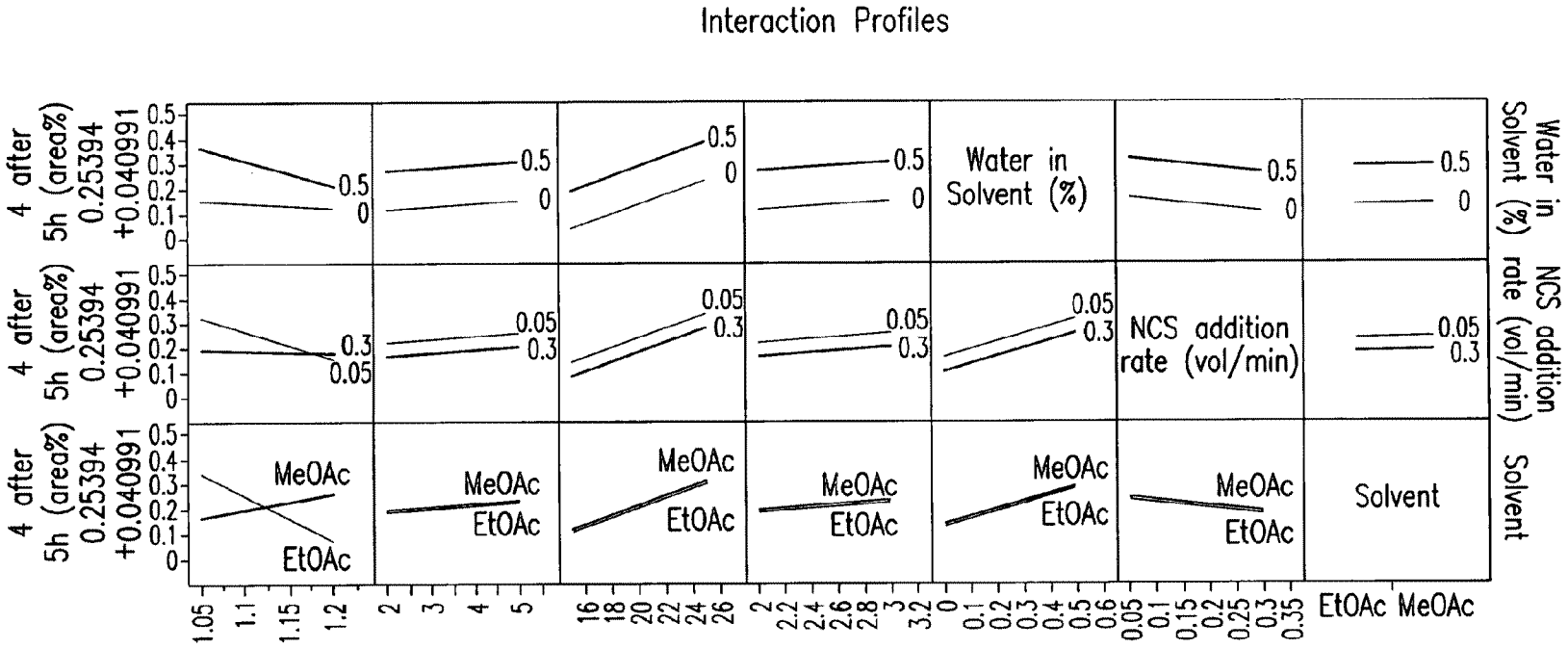
Figures 8A, 8B, 8C:
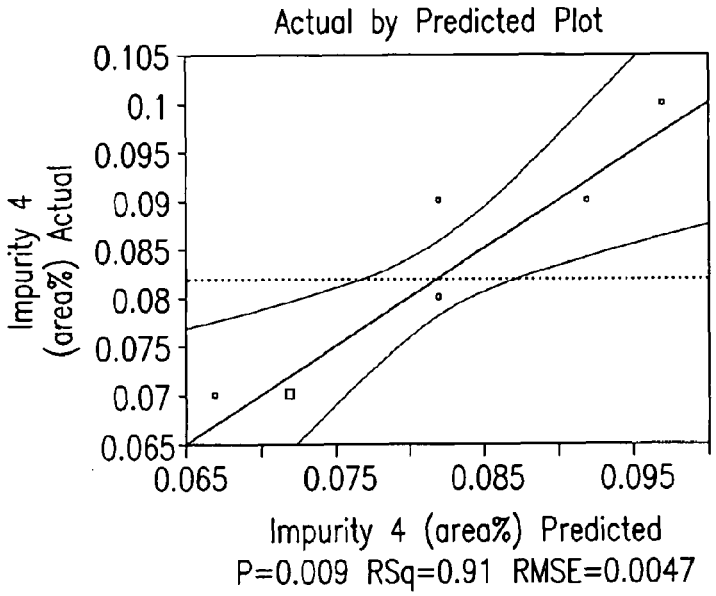
FIG. 8a shows an actual by predicted plot for the second design of experiments of FIG. 7.
FIG. 8b shows a summary of fit for the second design of experiments of FIG. 7.
FIG. 8c shows an analysis of variance for the second design of experiments of FIG. 7.
Figures 8D, 8E, 8F:
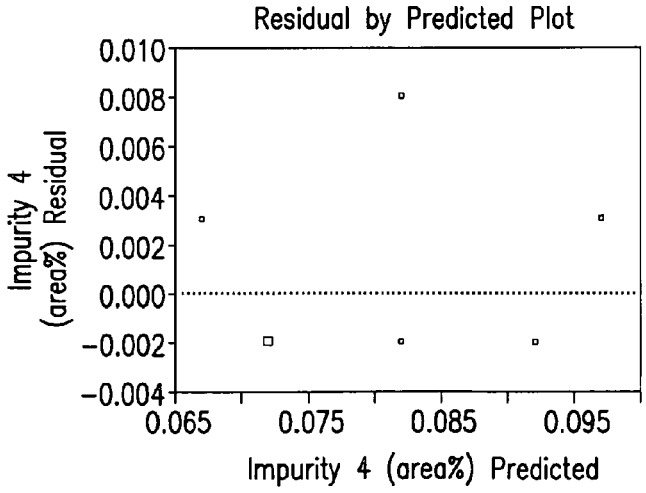
FIG. 8d shows a lack of fit for the second design of experiments of FIG. 7.
FIG. 8e shows parameter estimates for the second design of experiments of FIG. 7.
FIG. 8f shows a residual by predicted plot for the second design of experiments of FIG. 7.
Figure 8G:
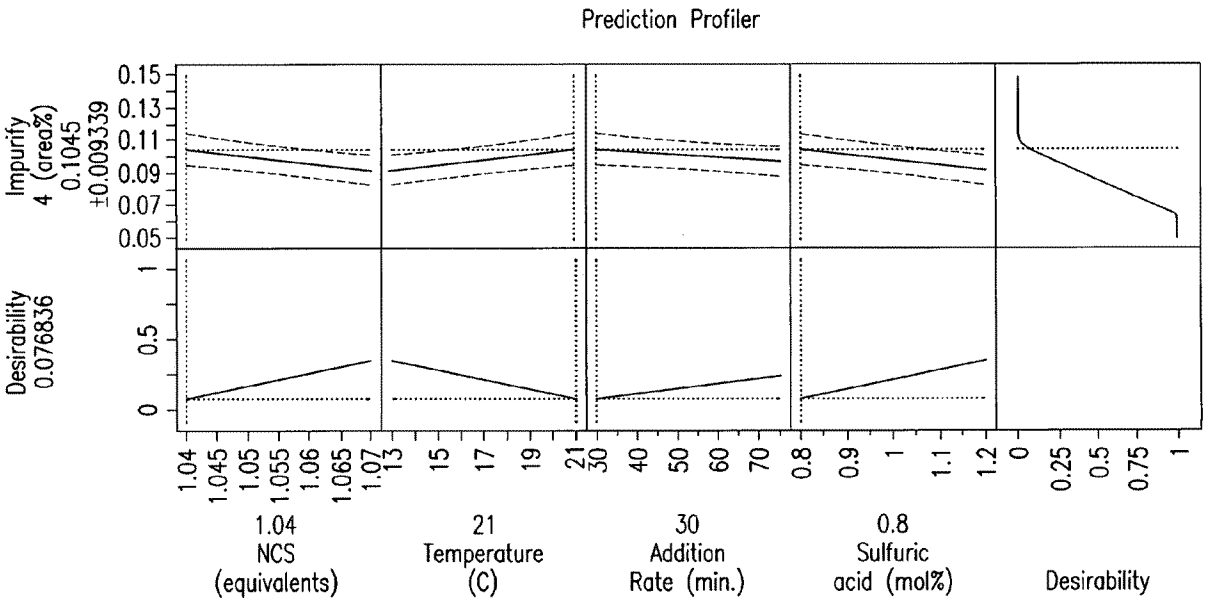
FIG. 8g shows a prediction profiler for the second design of experiments of FIG. 7.

After having established a good understanding of the critical parameters with respect to formation of this impurity, a second DoE study was initiated to test the robustness of the reaction in the anticipated process operating range. In this, a DoE study of resolution IV was designed with the following factors undergoing variation: temperature (13-21° C.), amount of NCS (1.04-1.07 eq.), NCS addition rate (30-75 min.) and $H_2SO_4$ (0.8-1.2 mol %). A total of 10 chlorination reactions were performed in a MultiMax™ reactor. In each case samples were quenched and saponified after passing the in-process control. The resulting area % of 4 was processed and analyzed using the DoE software. As anticipated, temperature, amount of NCS and $H_2SO_4$ had a statistically significant effect on the amount of impurity 4 in the studied parameter range. However, assuming the worst case scenario in the prediction profiler, impurity 4 has a value of 0.11 area %±0.01%, which is well within the acceptable limit that has been established from a toxicological batch of delafloxacin (FIG. 3).

Two subsequent kilo lab runs of this reaction confirmed the effectiveness of the parameter changes and material of high quality with impurity 4 levels of 0.07% were obtained after saponification.

In conclusion, we have successfully identified a dimer impurity which was detected during scale up of delafloxacin. Subsequent DoE experiments enabled us to identify means to control this impurity to acceptable levels in small scale as well as in kilo lab runs.

EXAMPLES

Example 1

1-(6-Amino-3,5-difluoro-pyridin-2-yl)-8-chloro-6-fluoro-7-(3-hydroxy-azetidin-1-yl)-4-oxo-1,4-dihydro-quinoline-3-carboxylic acid, 3, Improved procedure To a suspension of 1 (3.1 kg, 6.15 mol) in methyl acetate (8.6 kg) was added a solution of $H_2SO_4$ (5.9 g, 62 mmol) and NCS (0.88 kg, 6.46 mol) in methyl acetate (14.4 kg) at 10-17° C. within 45 min. The solution was stirred at 13-19° C. for 2 h, quenched with 1.6% aqueous $NaHCO_3$ (12.6 kg) and the organic layer was washed with 11% aqueous $Na_2SO_3$ (7 kg). The methyl acetate solution was solvent exchanged to 2-propanol at 50° C./vacuum, then a solution of KOH (1.1 kg, 19.7 mol) in water (24.8 kg) was added and the mixture was stirred at 55° C. for 3 h. 13% Aqueous acetic acid (2.6 kg) was added at 40° C. and the solution was seeded with 3 (27 g, 61 mmol). The suspension was stirred for 1 h at 40° C. and then 13% aqueous acetic acid (11.7 kg) was slowly added. After stirring an additional hour at 40° C. the suspension was cooled to room temperature, filtered, washed with water (41 kg) and dried at 60° C./vacuum to yield 3 as yellow crystals (2.5 kg, 91%). Isolated 3 had the same spectroscopic properties as reported.

Example 2

1-Amino-3-(azetidin-3-yloxy)-propan-2-ol-bis(N,N'-quinolone carboxylic acid), 4 3-Hydroxy-azetidine-1-carboxylic acid benzyl ester, 8

To a solution of azetidin-3-ol hydrochloride 7 (25 g, 0.23 mol) in water (150 mL) and THF (300 mL) was added $K_2CO_3$ (63.1 g, 0.46 mol). The mixture was stirred for 30 min. at 20-25° C. Then benzyl chloroformate (40.9 g, 0.24 mol) was added within 30 min. at 0-5° C. followed by stirring the mixture overnight at 20-25° C. THF was removed on a rotavap at 30° C./vacuum and the mixture was extracted with ethyl acetate (2×150 mL). The combined organic layer was washed with water (1×50 mL), dried over $Na_2SO_4$ and concentrated. The residue was purified by flash column chromatography on silica gel, eluting with ethyl acetate-heptanes 1:1 and 4:1 to yield 8 as a clear oil (47.3 g, 100%). $^1$H NMR (300 MHz, $CDCl_3$): δ 3.72 (1H, d, J=6.2 Hz), 3.85 (2H, dd, J=9.5, 4.4 Hz), 4.17 (2H, dd, J=9.5, 6.7 Hz), 4.49-4.57 (1H, m), 5.06 (2H, s), 7.31-7.38 (5H, m); 13C NMR (75 MHz, $CDCl_3$): δ 59.2, 61.6, 66.9, 127.9, 128.1, 128.5, 136.5, 156.6; IR: (film) 3406, 1686, 1438 $cm^{-1}$; ES-HRMS m/z: (M++1H) Calcd. for $C_{11}H_{14}NO_3$ 208.0968. Found 208.0967.

3-Oxiranylmethoxy-azetidine-1-carboxylic acid benzyl ester, 9

To a solution of 8 (30 g, 0.15 mol) in DMSO (250 mL) was slowly added a solution of NaOH (9.9 g, 0.25 mol) in water (195 mL) at 15-25 oC. Epichlorohydrin (93.8 g, 1.01 mol) was added and the mixture was stirred at 20-25° C. for 24 h. The mixture was diluted with water (300 mL) and extracted with ethyl acetate (2×150 mL). The combined organic layer was washed with water (2×50 mL), dried over $Na_2SO_4$ and concentrated. The residue was purified by flash column chromatography on silica gel, eluting with ethyl acetate-heptanes 3:2, yielding 9 as a clear oil (32.1 g, 84%). 1H NMR (300 MHz, $CDCl_3$): δ 2.60 (1H, dd, J=4.8, 2.6 Hz), 2.81 (1H, dd, J=4.9, 4.2 Hz), 3.09-3.16 (1H, m), 3.25 (1H, dd, J=11.4, 6.2 Hz), 3.68 (1H, dd, J=11.5, 2.5 Hz), 3.89-3.97 (2H, m), 4.15-4.24 (2H, m), 4.29-4.37 (1H, m), 5.09 (2H, s), 7.28-7.36 (5H, m); 13C NMR (75 MHz, $CDCl_3$): δ 44.2, 50.4, 56.7, 56.9, 66.7, 68.6, 70.0, 128.0, 128.1, 128.5, 136.6, 156.5; IR: (film) 2951, 1709, 1420 cm-1; ES-HRMS m/z: (M++1H) Calcd. for $C_{14}H_{18}NO_4$ 264.1230. Found 264.1230.

1-(6-Amino-3,5-difluoro-pyridin-2-yl)-7-[3-(1-benzyloxycarbonyl-azetidin-3-yloxy)-2-hydroxy-propylamino-]-8-chloro-6-fluoro-4-oxo-1,4-dihydroquinoline-3-carboxylic acid ethyl ester, 11

A mixture of 9 (19 g, 72.2 mmol) in conc. $NH_4OH$ (380 mL) and 7M $NH_3$ in MeOH (86 mL) was stirred for 5 h at room temperature. The clear solution was concentrated and azeotropically dried with toluene. The residual clear oil and 6 (20 g, 48.1 mmol) were dissolved in NMP (150 mL). N,N-diisopropylethylamine (12.4 g, 96.2 mmol) was added and the solution was stirred at 70° C. for 3 h. The solution was poured into 1N citric acid/ice (300 mL) and extracted with ethyl acetate (2×150 mL). The combined organic layer was washed with water (2×100 mL), dried over $Na_2SO_4$ and concentrated. The residue was purified by flash column chromatography on silica gel, eluting with ethyl acetate-heptanes 1:1 followed by ethyl acetate-MeOH 95:5, yielding 11 as a yellow foam (27.1 g, 83%). $^1$H NMR (300 MHz, $CDCl_3$): δ 1.35 (3H, t, J=7.1 Hz), 3.35-3.52 (4H, m), 3.62-3.77 (1H, m), 3.84-3.91 (2H, m), 3.95-4.08 (1H, m), 4.15 (2H, dd, J=9.3, 6.5 Hz), 4.23-4.30 (1H, m), 4.35 (2H, q, J=7.1 Hz), 4.85-5.13 (3H, br. s), 5.08 (2H, s), 7.18-7.25 (1H, m), 7.31-7.35 (5H, m), 7.99 (1H, dd, J=13.7, 3.1 Hz), 8.31 (1H, s); 13C NMR (75 MHz, $CDCl_3$): δ 14.4, 48.5 (d, JF=10 Hz), 56.6, 61.1, 66.9, 68.6, 69.3, 70.8, 107.2, 111.5, 112.6 (d, JF=24 Hz), 113.2 (m), 120.6, 128.0, 128.1, 128.5, 134.1 (d, JF=5 Hz), 134.7 (m), 136.5, 139.2 (d, JF=13 Hz), 144.9 (d, JF=253 Hz), 144.4 (d, JF=13 Hz), 145.6 (dd, JF=262, 4 Hz), 149.9 (d, JF=246 Hz), 150.0, 156.5, 164.7, 172.9; IR: (KBr) 2949, 1700, 1615 cm-1; ES-HRMS m/z: (M++1H) Calcd. for $C_{31}H_{30}ClF_3N_5O_7$ 676.1780. Found 676.1762.

1-(6-Amino-3,5-difluoro-pyridin-2-yl)-7-[3-(azetidin-3-yloxy)-2-hydroxy-propylamino]-8-chloro-6-fluoro-4-oxo-1,4-dihydro-quinoline-3-carboxylic acid ethyl ester, 12

To a slurry of 10% Pd on carbon (2.1 g) in MeOH (20 mL) was added a solution of 11 (13.7 g, 20.3 mmol) in MeOH (230 mL). The mixture was hydrogenated at 1 atm. for 1 h, filtered over Hyflo and evaporated yielding 12 as beige crystals (10.3 g, 93%). Mp. 148-152° C.; 1H NMR (300 MHz, DMSO-$d_6$): δ 1.27 (3H, t, J=7.1 Hz), 3.27 (1H, d, J=5.0 Hz), 3.28-3.80 (10H, m), 4.19 (1H, br. s), 4.21 (2H, q, J=7.1 Hz), 5.86 (1H, s), 6.74 (2H, s), 7.84 (1H, d, J=13.8 Hz), 7.94 (1H, dd, J=9.7, 9.0 Hz), 8.43 (1H, s); 13C NMR (75 MHz, $CDCl_3$): δ 14.1, 48.4 (d, JF=10 Hz), 53.6, 60.2, 68.4, 70.4 (d, JF=4 Hz), 72.1, 106.4 (d, JF=6 Hz), 111.0, 111.3 (d, JF=23 Hz), 113.6 (dd, JF=23, 21 Hz), 118.9 (d, JF=6 Hz), 133.8 (d, JF=13 Hz), 134.2, 139.5 (d, JF=12 Hz), 143.3 (dd, JF=248, 4 Hz), 145.0 (dd, JF=259, 5 Hz), 145.6 (d, JF=14 Hz), 149.3 (d, JF=245 Hz), 149.5, 163.5, 171.0; IR: (KBr) 1697, 1614, 1496, 1457 cm-1; ES-HRMS m/z: (M++1H) Calcd. for $C_{23}H_{24}ClF_3N_5O_5$ 542.1413. Found 542.1391.

1-Amino-3-(azetidin-3-yloxy)-propan-2-ol-bis(N,N'-quinolone diester), 13

A solution of 12 (9.6 g, 17.7 mmol), 6 (7.8 g, 18.6 mmol) and N,N-diisopropylethylamine (4.6 g, 35.4 mmol) in NMP (150 mL) was stirred at 55° C. for 3 h. The solution was poured into 1N citric acid/ice (300 mL) and extracted with ethyl acetate (3×100 mL). The combined organic layer was washed with water (2×100 mL), dried over $Na_2SO_4$ and concentrated. The residue was purified by flash column chromatography on silica gel, eluting with ethyl acetate-MeOH 95:5. The obtained yellow foam was crystallized with $CH_2Cl_2$-MeOH 9:1 (160 mL), yielding 13 as beige crystals (11.8 g, 71%). Mp. 184-187° C.;

1H NMR (300 MHz, DMSO-$d_6$): δ 1.26 (6H, t, J=7.1 Hz), 3.29-3.48 (3H, m), 3.49-3.62 (1H, m), 3.73-3.82 (1H, m), 4.12-4.30 (3H, m), 4.21 (4H, q, J=7.1 Hz), 4.52-4.65 (2H, m), 5.13-5.22 (1H, m), 5.83-5.92 (1H, m), 6.72 (4H, s), 7.73 (1H, d, J=13.9 Hz), 7.82 (1H, d, J=13.9 Hz), 7.92 (1H, t, J=9.6 Hz), 7.93 (1H, t, J=8.7 Hz), 8.41 (2H, s); 13C NMR (75 MHz, $CDCl_3$): δ 12.3 (2×), 46.4 (d, JF=11 Hz), 58.4 (2×), 61.9 (2×), 66.7, 67.3 (d, JF=4 Hz), 69.1, 103.4 (d, JF=6 Hz), 104.6 (d, JF=6 Hz), 108.7 (d, JF=23 Hz), 109.2, 109.4 (d, JF=23 Hz), 109.5, 111.7 (dd, JF=25, 24 Hz), 111.8 (dd, JF=25, 24 Hz), 117.1 (d, JF=7 Hz), 117.8 (d, JF=6 Hz), 132.1 (dd, JF=17, 4 Hz), 132.2, 132.5, 133.5, 137.7 (d, JF=12 Hz), 139.4 (d, JF=12 Hz), 141.0 (dd, JF=247, 5 Hz), 141.5 (dd, JF=248, 5 Hz), 143.0 (dd, JF=259, 5 Hz), 143.3 (dd, JF=259, 5 Hz), 143.8 (2×, d, JF=15 Hz), 147.5 (d, JF=245 Hz), 147.7, 147.8, 148.1 (d, JF=247 Hz), 161.7 (2×), 169.1, 169.2; IR: (KBr) 1728, 1615, 1491, 1448 cm-1; ES-HRMS m/z: (M++1H) calcd. for $C_{40}H_{33}Cl_2F_6N_8O_8$ 937.1697. Found 937.1696.

1-Amino-3-(azetidin-3-yloxy)-propan-2-ol-bis(N,N'-quinolone carboxylic acid), 4

To a suspension of 13 (17.0 g, 18.1 mmol) in 2-propanol (75 mL) was added a 1N KOH solution (127 mL, 126.7 mmol). After stirring the mixture at 55° C. for 3.5 h, the solution was cooled to 30° C. and a solution of AcOH (12.4 g, 206.5 mmol) dissolved in water (94 mL) was added within 1 h. The suspension was stirred at room temperature for 2 h, filtered, washed with water (3×40 mL) and dried at 50° C./vacuum, yielding 4 as yellow crystals (15.7 g, 98%). Mp. 198-205 oC (decomp.); $^1$H NMR (300 MHz, DMSO-d6): δ 3.28-3.45 (2H, m), 3.45-3.78 (2H, m), 3.79-3.88 (1H, m), 4.16-4.33 (3H, m), 4.61-4.75 (2H, m), 5.25 (1H, br. s), 6.23-6.35 (1H, m), 6.76 (4H, s), 7.79 (1H, d, J=13.7 Hz), 7.90 (1H, d, J=13.8 Hz), 7.93 (2H, dd, J=9.7, 2.4 Hz), 8.70 (1H, s), 8.71 (1H, s), 14.59 (2H, br. s); 13C NMR (75 MHz, $CDCl_3$): □ 48.1 (d, JF=11 Hz), 63.8, 68.4, 69.0 (d, JF=5 Hz), 70.6 (d, JF=6 Hz), 104.5 (d, JF=6 Hz), 105.9 (d, JF=7 Hz), 107.8, 108.2, 109.8 (d, JF=23 Hz), 110.8 (d, JF=23 Hz), 113.4 (d, JF=23 Hz), 113.7 (d, JF=23 Hz), 115.8 (d, JF=8 Hz), 116.6 (d, JF=8 Hz), 133.3 (dd, JF=14, 3 Hz), 133.5 (dd, JF=14, 4 Hz), 134.8, 135.9, 141.0 (d, JF=12 Hz), 142.1 (d, JF=12 Hz), 142.8 (dd, JF=249, 5 Hz), 143.3 (dd, JF=249, 5 Hz), 145.1 (dd, JF=259, 5 Hz), 145.4 (dd, JF=260, 5 Hz), 145.6 (2×, d, JF=15 Hz), 149.5 (d, JF=248 Hz), 150.1 (2×), 150.2 (d, JF=249 Hz), 164.7, 164.8, 175.8 (d, JF=3 Hz), 175.9 (d, JF=3 Hz); IR: (KBr) 1727, 1622, 1489, 1439 cm-1; ES-HRMS m/z: (M++1H) Calcd. for $C_{36}H_{25}C_{12}F_6N_8O_8$ 881.1071, found 881.1090.

Additional Experimental Materials

Experimental tables and analyses of the DoE studies are further provided in FIG. 4, FIGS. 5a, 5b, 5c, 5d, 5e, and 5f, FIGS. 6a and 6b, FIG. 7, and FIGS. 8a, 8b, 8c, 8d, 8e, 8f, and 8g.

Formulation and Administration

The compounds of the present invention can be practiced by delivering the compounds of the present invention using any suitable carrier. The dose of active compound, mode of administration and use of suitable carrier will depend upon the intended patient or subject and the targeted microorganism, e.g., the target bacterial organism. The formulations, both for human medical use and veterinary use, of compounds according to the present invention typically include such compounds in association with a pharmaceutically acceptable carrier.

The carrier should be "acceptable" in the sense of being compatible with compounds of the present invention and not deleterious to the recipient. Pharmaceutically acceptable carriers, in this regard, are intended to include any and all solvents, dispersion media, coatings, absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Solutions or suspensions can include the following components: a sterile diluent such as water, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

A wide variety of formulations and administration methods, including, e.g., intravenous formulations and administration methods can be found in S. K. Niazi, ed., Handbook of Pharmaceutical Formulations, Vols. 1-6 [Vol. 1 Compressed Solid Products, Vol. 2 Uncompressed Drug Products, Vol. 3 Liquid Products, Vol. 4 Semi-Solid Products, Vol. 5 Over the Counter Products, and Vol. 6 Sterile Products], CRC Press, Apr. 27, 2004.

Useful solutions for oral or parenteral administration can be prepared by any of the methods well known in the pharmaceutical art, described, for example, in Remington's Pharmaceutical Sciences, 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.1 to about 100 mg/kg of body weight/day, more preferably from about 1.0 to about 50 mg/kg of body weight/day. The amount administered will also likely depend on such variables as the type of surgery or invasive medical procedure, the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present invention according to the methods of the present invention.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e. minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

All percentages and ratios used herein, unless otherwise indicated, are by weight. The percent dimeric impurity is on an area percent basis, typically as quantified by analytical HPLC.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Formulation Examples

Formulation for Intravenous Administration

| Ingredients | Amount |
|---|---|
| Antimicrobial Compound | 0.1-1500 total mg |
| Dextrose, USP | 50 mg/ml |
| Sodium citrate, USP | 1.60-1.75 mg/ml |
| Citric Acid, USP | 0.80-0.90 mg/ml |
| Water, USP | q.s |

This formulation for intravenous administration is formulated by heating water for injection to about 60° C. Next the sodium citrate, citric acid and dextrose are added and stirred until dissolved. A solution or aqueous slurry of the antimicrobial compound is added to the previous mixture and stirred until dissolved. The mixture is cooled to 25° C. with stirring. The pH is measured and adjusted if necessary. Lastly the mixture is brought to the desired volume, if necessary, with water for injection. The mixture is filtered, filled into the desired container (vial, syringe, infusion container, etc.), over wrapped and terminally moist heat sterilized.

This formulation is useful for intravenous administration, either bolus or infusion, to a patient.

Tablets for Oral Administration

| Ingredients | Per Tablet | Per 4000 Tablets |
|---|---|---|
| Antimicrobial Compound | 0.1-1500 mg | 0.4-6000 g |
| Anhydrous Lactose, NF | 110.45 mg | 441.8 g |
| Microcrystalline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The antimicrobial compound (any of the compounds equivalent to the desired delivery strength, e.g., 50 to 1500 mg per tablet) is premixed with ⅓ of the microcrystalline cellulose NF and ½ of the anhydrous lactose NF in a ribbon blender for 5 minutes at 20 RPM. To the premix is added the remaining ⅔ of the microcrystalline cellulose NF and the remaining ½ of the anhydrous lactose NF. This is blended for 10 minutes at 20 RPM. Crosscarmellose sodium is added to the blended powders and mixed for 5 minutes at 20 RPM. Finally the magnesium stearate is added to the mixture by passing through a 90 mesh screen and blended for an additional 5 minutes at 20 RPM. The lubricated mixture is compressed to provide tablets of 500 mg active ingredient.

These tablets are useful for oral administration to a patient.

Incorporation By Reference

The entire disclosure of each of the patent documents, including certificates of correction, patent application documents, scientific articles, governmental reports, websites, and other references referred to herein is incorporated by reference in its entirety for all purposes. In case of a conflict in terminology, the present specification controls.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A process for preparing a quinolone compound comprising the step of reacting a des-chloro quinolone compound or a pharmaceutically acceptable salt or ester thereof with a chlorinating agent and an acid, wherein the molar ratio of the acid to des-chloro quinolone is from about [0.007] *0.008* to about [0.02] *0.012*, and wherein less than about [0.40%] *0.35%* of dimeric impurity on an area percent basis of the quinolone is produced*, wherein the quinolone compound is 1-(6-amino-3,5-difluoropyridin-2-yl)-8-chloro-6-fluoro-7-(3-hydroxyazetidin-1-yl)-4-oxo-1,4-dihydroquinoline-3-carboxylic acid or a pharmaceutically acceptable salt or ester thereof and the des-chloro quinolone compound is 1-(6-amino-3,5-difluoropyridin-2-yl)-6-fluoro-7-(3-hydroxy-azetidin-1-yl)-4-oxo-1,4-dihydroquinoline-3-carboxylic acid or a pharmaceutically acceptable salt or ester thereof, and wherein the dimeric impurity is 1-amino-3-(azetidin-3-yloxy)-propan-2-ol-bis(N,N'-quinolone carboxylic acid), or a pharmaceutically acceptable salt or ester thereof.*

[2. A process according to claim 1 wherein the quinolone compound is 1-(6-Amino-3,5-difluoropyridin-2-yl)-8-chloro-6-fluoro-7-(3-hydroxyazetidin-1-yl)-4-oxo-1,4-dihydroquinoline-3-carboxylic acid or a pharmaceutically acceptable salt or ester thereof and the des-chloro quinolone compound is 1-(6-amino-3,5-difluoropyridin-2-yl)-6-fluoro-7-(3-hydroxy-azetidin-1-yl)-4-oxo-1,4-dihydroquinoline-3-carboxylic acid or a pharmaceutically acceptable salt or ester thereof.]

[3. A process according to claim 2 wherein the dimeric impurity is 1-Amino-3-(azetidin-3-yloxy)-propan-2-ol-bis (N,N'-quinolone carboxylic acid), or a pharmaceutically acceptable salt or ester thereof.]

4. A process according to claim 1 wherein the chlorinating agent is N-chlorosuccinimide.

5. A process according to claim 1 wherein the acid is selected from the group consisting of sulfuric acid, hydrochloric acid, hydrobromic acid, phosphoric acid, trifluoroacetic acid, triflic acid, methanesulfonic acid, p-toluenesulfonic acid, or perchloric acid, and mixtures thereof.

6. A process according to claim 1 wherein the acid is sulfuric acid.

7. A process according to claim 1 where the reaction is run at a temperature from about 0° C. to about 30° C.

8. A process according to claim 1 wherein the molar ratio of [N-chlorosuccinimide] *the chlorinating agent* to des-chloro quinolone is greater than about 1.

9. A process according to claim 1 using an acetate ester as a solvent.

10. A process according to claim 9 wherein said acetate ester is selected from the group consisting of methyl acetate, ethyl acetate, and mixtures thereof.

11. A process according to claim 9 wherein said acetate ester is methyl acetate.

12. A process according to claim 1 comprising the further step of reacting the quinolone compound with a base.

13. A process according to claim 12 wherein the base is a hydroxide base.

14. A process according to claim 13 wherein the hydroxide base is selected from the group consisting of sodium hydroxide, potassium hydroxide, lithium hydroxide, barium hydroxide, and mixtures thereof.

15. A process according to claim 14 wherein the hydroxide base is potassium hydroxide.

16. A process according to claim 12 using a mixture of isopropanol and water as a solvent.

17. A process according to claim 1 wherein said process is a commercial scale process.

18. A composition comprising the quinolone compound [1-(6-Amino-3,5-difluoropyridin-2-yl)-8-chloro-6-fluoro-7-(3-hydroxyazetidin-1-yl)-4-oxo-1,4-dihydroquinoline-3-carboxylic] *1-(6-amino-3,5-difluoropyridin-2-yl)-8-chloro-6-fluoro-7-(3-hydroxyazetidin-1-yl)-4-oxo-1,4-dihydroquinoline-3-carboxylic* acid or *a pharmaceutically acceptable* salt or ester thereof having less than about [0.40%] *0.35*% of the compound [1-Amino-3-(azetidin-3-yloxy)-propan-2-ol-bis(N,N'-quinolone] *1-amino-3-(azetidin-3-yloxy)-propan-2-ol-bis(N,N'-quinolone* carboxylic acid), or a pharmaceutically acceptable salt or ester thereof *on an area percent basis of the quinolone*.

19. A composition according to claim 18 wherein said composition is a commercial scale composition.

20. The process of claim 1 [or 2], wherein the molar ratio of chlorinating agent to des-chloro quinolone is from about 1.05 to about 1.2.

21. The process of claim 1 [or 2], wherein the molar ratio of chlorinating agent to des-chloro quinolone is from about 1.04 to about 1.07.

[22. The process of claim 1 or 2, wherein the molar ratio of acid to des-chloro quinolone is from about 0.008 to about 0.012.]

* * * * *